United States Patent
Dorner et al.

(10) Patent No.: US 10,650,354 B2
(45) Date of Patent: *May 12, 2020

(54) SYSTEM AND METHOD FOR TRANSACTING LEAD AND SCHEDULED APPOINTMENT RECORDS

(71) Applicant: SetSchedule IP Holdings, LLC, Irvine, CA (US)

(72) Inventors: Yehuda Dorner, Irvine, CA (US); Roy Dekel, Irvine, CA (US)

(73) Assignee: SetSchedule IP Holdings, LLC, Irvine, CA (US)

( * ) Notice: Subject to any disclaimer, the term of this patent is extended or adjusted under 35 U.S.C. 154(b) by 196 days.

This patent is subject to a terminal disclaimer.

(21) Appl. No.: 15/899,306

(22) Filed: Feb. 19, 2018

(65) Prior Publication Data

US 2018/0174113 A1 Jun. 21, 2018

Related U.S. Application Data

(63) Continuation of application No. 15/097,568, filed on Apr. 13, 2016, now Pat. No. 9,934,490.

(Continued)

(51) Int. Cl.
   *G06Q 10/10* (2012.01)
   *G06Q 50/16* (2012.01)

(52) U.S. Cl.
   CPC ....... *G06Q 10/1095* (2013.01); *G06Q 50/167* (2013.01)

(58) Field of Classification Search
   CPC .......... G06F 17/30867; G06Q 10/1095; G06Q 30/0281; G06Q 50/16
   See application file for complete search history.

(56) References Cited

U.S. PATENT DOCUMENTS

| 6,385,541 B1 | 5/2002 | Blumberg |
| 6,937,853 B2 | 8/2005 | Hall |

(Continued)

FOREIGN PATENT DOCUMENTS

| EP | 1903491 A1 | 3/2008 |
| EP | 2747031 A1 | 6/2014 |

*Primary Examiner* — Matthew S Gart
*Assistant Examiner* — Stephen S Swartz
(74) *Attorney, Agent, or Firm* — Jafari Law Group, Inc.

(57) ABSTRACT

The present invention is generally a system and method for transacting lead records and scheduled appointment records concerning business opportunities in the real estate industry. The transactions may include offering the scheduled appointment records or lead records for sale, as well as auctioning the records. Several software modules may be provided to: receive, categorize, qualify, and distribute leads that mature into transactional opportunities; determine the geographic location of real estate client users and transactional opportunities near a user's location or selected region; facilitate management of each transactional opportunity by the client user; facilitate management of each transactional opportunity by the service provider; and various other functions and services consistent with the present system and method. Moreover, an exchange platform may be implemented with the present system whereby affiliates of the service provider may introduce their own leads and sell them to subscribers.

20 Claims, 26 Drawing Sheets

Related U.S. Application Data

(60) Provisional application No. 62/272,429, filed on Dec. 29, 2015.

(56) References Cited

U.S. PATENT DOCUMENTS

| | | |
|---|---|---|
| 7,016,866 B1 | 3/2006 | Chin |
| 7,415,356 B1 | 8/2008 | Gowda |
| 7,673,248 B2 | 3/2010 | Narayanaswami |
| 7,848,966 B2 | 12/2010 | Charuk |
| 7,970,674 B2 | 6/2011 | Cheng |
| RE43,068 E | 1/2012 | Woodard |
| 8,095,434 B1 | 1/2012 | Puttick |
| 8,140,421 B1 | 3/2012 | Humphries |
| 8,510,349 B1 | 8/2013 | Puttick |
| 8,515,839 B2 | 8/2013 | Ma |
| 8,667,017 B1 | 3/2014 | Forney |
| 8,676,680 B2 | 3/2014 | Humphries |
| 8,902,042 B2 | 12/2014 | Davis |
| 8,978,006 B2 | 3/2015 | Hirsch |
| 8,983,927 B2 | 3/2015 | Rao |
| 9,137,640 B2 | 9/2015 | Eaton |
| 2002/0022980 A1 | 2/2002 | Mozayeny |
| 2002/0035493 A1 | 3/2002 | Mozayeny |
| 2002/0046069 A1 | 4/2002 | Mozayeny |
| 2002/0046077 A1 | 4/2002 | Mozayeny |
| 2003/0065545 A1 | 4/2003 | Lunn |
| 2006/0026032 A1 | 2/2006 | Higgins |
| 2006/0256109 A1 | 11/2006 | Acker |
| 2006/0265312 A1 | 11/2006 | Rascoff |
| 2007/0050342 A1 | 3/2007 | Inkinen |
| 2007/0156758 A1 | 7/2007 | Adiga |
| 2007/0185727 A1 | 8/2007 | Ma |
| 2007/0185906 A1 | 8/2007 | Humphries |
| 2007/0198278 A1 | 8/2007 | Cheng |
| 2007/0203776 A1 | 8/2007 | Austin |
| 2008/0001839 A1 | 1/2008 | Wei |
| 2008/0077458 A1 | 3/2008 | Anderson |
| 2008/0303811 A1 | 12/2008 | Van Luchene |
| 2009/0240550 A1* | 9/2009 | McCarty ........... G06Q 10/06311 705/7.13 |
| 2009/0265229 A1 | 10/2009 | Sidhu |
| 2010/0241523 A1 | 8/2010 | Raichura |
| 2011/0167366 A1 | 7/2011 | Wagner |
| 2011/0257986 A1 | 10/2011 | Deanne |
| 2011/0313840 A1 | 12/2011 | Mason |
| 2012/0330714 A1 | 12/2012 | Malaviya |
| 2012/0330715 A1 | 12/2012 | Malaviya |
| 2012/0330719 A1 | 12/2012 | Malaviya |
| 2013/0073377 A1 | 3/2013 | Heath |
| 2013/0304654 A1 | 11/2013 | Ma |
| 2013/0305144 A1 | 11/2013 | Jackson |
| 2013/0305145 A1 | 11/2013 | Jackson |
| 2014/0025657 A1 | 1/2014 | Dorfman |
| 2014/0180936 A1 | 6/2014 | Ma |
| 2014/0236350 A1 | 8/2014 | Woodard |
| 2014/0236845 A1 | 8/2014 | Humphries |
| 2014/0249878 A1* | 9/2014 | Kaufman ........... G06Q 10/1095 705/7.19 |
| 2014/0316999 A1 | 10/2014 | Cheng |
| 2015/0106006 A1 | 4/2015 | Najafi |
| 2015/0193892 A1 | 7/2015 | Bond |
| 2015/0235306 A1 | 8/2015 | Sabella |
| 2016/0093007 A1 | 3/2016 | Richardson |

* cited by examiner

FIG. 2(b)

| LEAD RECORD | | | | |
|---|---|---|---|---|
| Lead_ID 221 | Property_ID 222 | Owner_ID 223 | Source_ID 224 | CRM_ID 225 |
| Lead_Type 226 | Lead_Tier 227 | Lead_Price 228 | Dispatch_Info 229 | Lead_Status 230 |

— 211

| SCHEDULED APPOINTMENT RECORD | | | | |
|---|---|---|---|---|
| Lead_ID 221 | Property_ID 222 | Owner_ID 223 | Source_ID 224 | CRM_ID 225 |
| Lead_Type 226 | Lead_Tier 227 | Lead_Price 228a | Dispatch_Info 229 | Lead_Status 230 |
| Scheduled_Date-Time-Place | | | | 231 |

— 212

| OFFER RECORD | | | | |
|---|---|---|---|---|
| Offer_ID 232 | Lead_ID 221 | Offer_Type 233 | Offer_Timer 234 | Offer_Cap 235 |
| Agent_ID 236 | Lead_Tier 227 | Lead_Price 228a | Scheduled_Date-Time-Place | 231 |
| Offer_Information | | | | 237 |

— 213

| OFFER RECORD | | | | |
|---|---|---|---|---|
| Offer_ID 238 | Lead_ID 239 | Offer_Type 240 | Offer_Timer 241 | Offer_Cap 242 |
| Role_ID 243 | Lead_Tier 244 | Lead_Price 245 | Offer_Information | 246 |

— 214

SYSTEM AND METHOD FOR TRANSACTING LEAD AND SCHEDULED APPOINTMENT RECORDS

PRIORITY NOTICE

This application is a continuation of pending U.S. Nonprovisional application Ser. No. 15/097,568, filed on Apr. 13, 2016, which claims priority under 35 U.S.C. § 119(e) to U.S. Provisional Patent Application Ser. No. 62/272,429 filed on Dec. 29, 2015, the disclosure of each incorporated herein by reference in their entirety.

TECHNICAL FIELD OF THE INVENTION

The present invention relates in general to a system and method for transacting lead and scheduled appointment records, and more specifically, to a system and method for facilitating transactions of scheduled appointments and leads concerning business opportunities in the real estate industry.

COPYRIGHT AND TRADEMARK NOTICE

A portion of the disclosure of this patent application may contain material that is subject to copyright protection. The owner has no objection to the facsimile reproduction by anyone of the patent documents or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Traditionally, purchasing real estate requires prospective buyers and sellers to transact through a real estate professional—typically a licensed individual or entity such as a licensed real estate agent, broker, or realtor—referred hereinafter simply as "realtor". With an ever growing real estate industry, the number of realtors has similarly increased. As such, realtors are finding that keeping a competitive edge against the tremendous number of licensed individuals or entities is increasingly difficult.

Realtors interested in pursuing business opportunities in the real estate industry face numerous challenges. With more professionals available in a particular area, prospective buyers and prospective sellers may choose from a plethora of available licensed professional to help them with real estate transactions. Moreover, the World Wide Web has made the largest real estate companies and the more independent licensed individuals, seemingly equally accessible. Hence, there is a growing need for maintaining a competitive edge in the real estate industry.

One of the challenges that realtors face is the procurement of new prospects and new business opportunities or leads. While the Internet may make a realtor's contact information widely available to the public, receiving quality leads typically means having to spend considerable resources sifting through requests with low or no potential of turning into a successful transaction. Similarly, the vast number of competing realtors and flood of advertising information makes branding increasingly difficult. Furthermore, even where a good referral system is implemented, turning those referrals into successful transactions and turning current business into repeat business remains a challenge.

Therefore, there are several challenges with the current state of the real estate industry that have not been adequately addressed by the prior art. These challenges persist because a need to provide a system and method for facilitating real estate transactions has not been adequately met. As such, a new and improved system that facilitates transacting business opportunities in the real estate industry is desirable, and it is to these ends that the present invention has been developed.

SUMMARY OF THE INVENTION

To minimize the limitations in the prior art, and to minimize other limitations that will be apparent upon reading and understanding the present specification, the present invention describes a system and method for facilitating transactions of scheduled appointment and lead records concerning business opportunities in the real estate industry. The service provider may provide a mobile application platform to real estate client users, or realtor-clients, who may access different transactional opportunities in the form of leads or pre-scheduled appointments, which have been converted into trackable records such as lead records or scheduled appointment records, with interested buyers or sellers of real property.

A system for transacting scheduled appointments, in accordance with an exemplary embodiment of the present invention, comprises: a server including a network interface for communicating with one or more client devices, and one or more processors configured to: receive qualified lead information concerning one or more real estate transaction opportunities; generate a scheduled appointment record from the qualified lead information; match a geographic location relevant to a user with the geographic location associated with the scheduled appointment record; provide the scheduled appointment record to a client device associated with the user; and register a transaction with the client device concerning the scheduled appointment record.

A system for transacting scheduled appointments, in accordance with another exemplary embodiment of the present invention, comprises: a server including a network interface for communicating with one or more client devices, and one or more processors configured to: generate an offer for a scheduled appointment record concerning a proposed transaction; provide the offer for the scheduled appointment record to a client device; register a transaction with the client device concerning an acceptance of the offer; assign a first predetermined time period to the scheduled appointment record; monitor, via the client device, a progress status associated with the proposed transaction; determine whether the first time period has lapsed prior to a consummation of the proposed transaction; and either: register with the client device the consummation of the proposed transaction; or assign a second predetermined time period to the scheduled appointment record if the first predetermined period has lapsed prior to the consummation of the proposed transaction.

A method for transacting scheduled appointments, in accordance with practice of an exemplary embodiment of the present invention, comprises: receiving qualified lead information concerning one or more real estate transaction opportunities; generating a scheduled appointment record from the qualified lead information; providing the client device with the scheduled appointment record; and registering a transaction with the client device concerning the scheduled appointment record.

A method for transacting scheduled appointments, in accordance with practice of another exemplary embodiment of the present invention, comprises: generating an offer for a scheduled appointment record concerning a proposed transaction; providing the offer for the scheduled appointment record to a client device; registering a transaction with the client device concerning an acceptance of the offer; assigning a first predetermined time period to the scheduled appointment record; monitoring, via the client device, a progress status associated with the proposed transaction; determining whether the first time period has lapsed prior to a consummation of the proposed transaction; and either: registering with the client device the consummation of the proposed transaction; or assigning a second predetermined time period to the scheduled appointment record if the first predetermined period has lapsed prior to the consummation of the proposed transaction.

It is an objective of the present invention to facilitate the transacting of scheduled events concerning real estate transactions.

It is another objective of the present invention to provide a system that connects realtors to individuals or entities interested in consummating a real estate transaction.

It is yet an another objective of the present invention to provide a system that generates multiple opportunities from a single lead concerning a real estate transaction.

It is yet an another objective of the present invention to provide a system that facilitates data mining or aggregation opportunities in the real estate industry.

It is yet another objective of the present invention to provide a system that may implement an exchange platform for transacting lead records and scheduled appointment records.

These and other objectives, advantages and features of the present invention are described herein with specificity so as to make the present invention understandable to one of ordinary skill in the art.

BRIEF DESCRIPTION OF DRAWINGS

Elements in the figures have not necessarily been drawn to scale in order to enhance their clarity and improve understanding of these various elements and embodiments of the present invention. Furthermore, elements that are known to be common and well understood to those in the industry are not depicted in order to provide a clear view of the various embodiments of the invention.

FIG. 2(b) illustrates exemplary embodiments of data structures for a lead record, a scheduled appointment record, and an offer record.

DESCRIPTION OF THE INVENTION

Figure 1A:
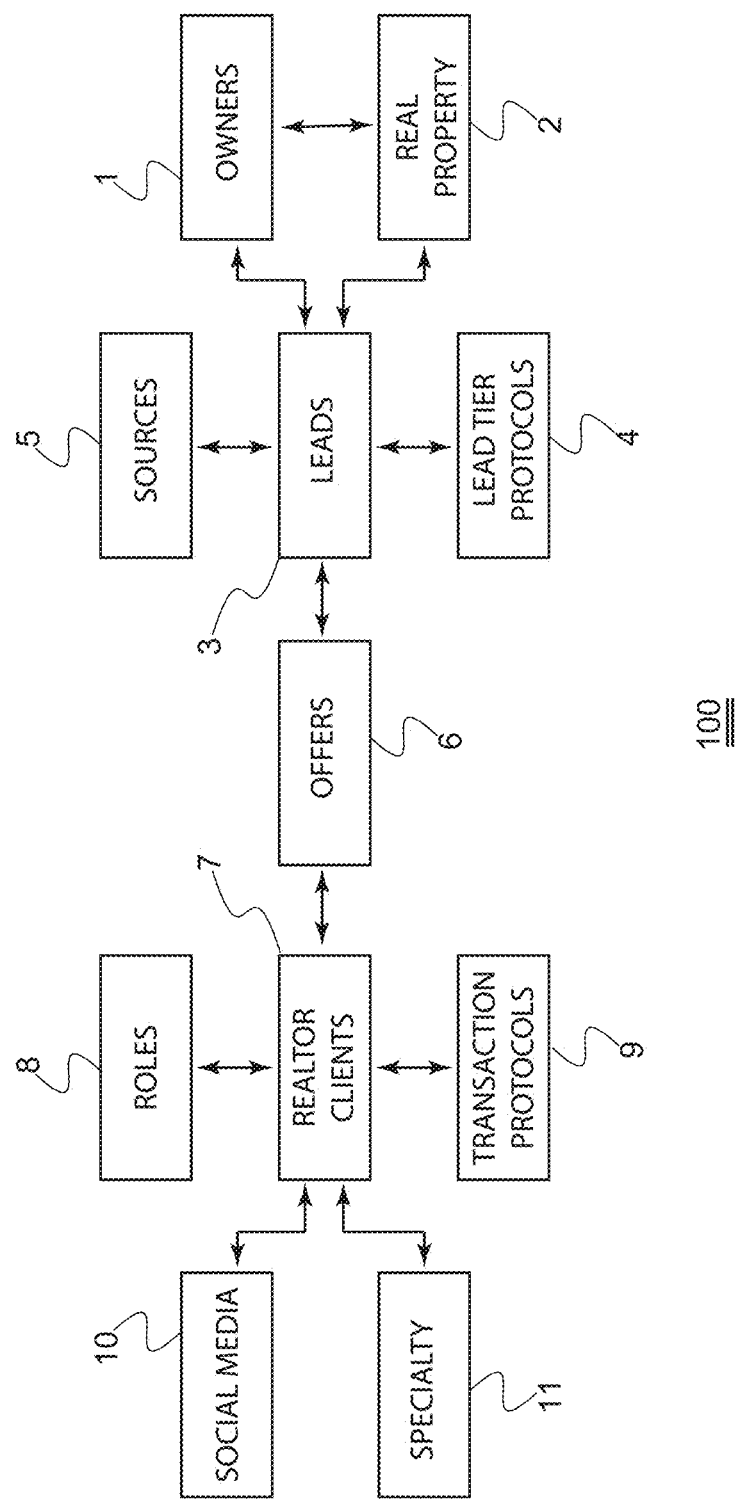
FIG. 1(a) illustrates an entity relationship diagram of a business model that may be practiced in accordance with the present invention.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention. Wherever possible, the same reference numbers are used in the drawings and the following description to refer to the same or similar elements. While embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims.

In the present specification, the term seller may include any individual, group of individuals, or legal entity that is interested in selling real property. A buyer may refer to any individual, group of individuals, or legal entity that is interested in purchasing real property. A realtor may refer to any individual, group of individuals, or entity that is licensed to sell, purchase, lease, or otherwise facilitate others with consummating real estate transactions. Transactional opportunities may refer to leads, qualified leads, or scheduled appointments concerning proposed transactions in real estate. Leads may refer to an opportunity to list real property with a realtor—and may include general or personal information of an interested buyer, an interested seller, real property information, or any marketing, advertising, or other information concerning a real estate transaction, including a party's interest in buying, selling, leasing, or renting real property. Qualified leads may refer to leads that have been automatically or systematically qualified as leads suitable for generating a lead record or a scheduled appointment record. Lead records may be records containing lead or qualified lead information. Scheduled appointment records may be records containing lead or qualified lead information, which have been confirmed and generated with specific scheduled dates and times for pursuing a real estate transaction. Users or realtor-clients may refer to realtors, or non-realtor users of the system, who may access the system's server via an application to receive offers concerning qualified leads or scheduled appointment records.

Generally, the present invention involves a system and method for facilitating transactions concerning leads and scheduled appointments in the real estate industry. The system may be configured to receive information concerning transactional opportunities, or leads, pertaining to one or more parties interested in pursuing a real estate transaction. Each lead may be followed-up, verified, or qualified to ensure that real parties interested in consummating a real estate transaction are willing and able to, for example, schedule a particular time and date to meet with a realtor. Once a lead has been qualified, a record of that lead may be generated and stored as a qualified lead record. Similarly, qualified leads may be utilized to generate scheduled appointment records, which include an agreed-upon time and date for the interested party to meet with a realtor-client of the system. These lead records and scheduled appointment records may then be offered to realtor-clients of the system via a mobile device application that allows an interested realtor-client to purchase or bid on one or more records. Furthermore, an exchange platform may be implemented so that affiliates or third-party participants may offer their own lead records to the realtor-clients of the system.

In exemplary embodiments, a system and method for transacting qualified lead records and scheduled appointment records works preferably with a membership-based business model that dictates a realtor-client's access to the lead records and scheduled appointment records offered by a service provider. Such business model is facilitated via a computer-readable medium configured to procure, cultivate, and distribute offers concerning such transactional opportunities.

For example, an exemplary system may comprise of a computer readable medium, such as a server, configured to access a database of realtor-clients and real estate related leads from buyers, sellers, renters, lessors, or other realtors. These leads may be autonomously or systematically analyzed to identify viable transactional opportunities in order to generate offers based on lead records or schedule appointment records that include a specific interested party, date, and time for an appointment concerning a proposed real estate transaction. In some embodiments, each lead or scheduled appointment record may be provided to a plurality of realtor-clients via a plurality of client devices configured with a graphical user interface or GUI that displays offer records in one or more geographic locations relevant to each realtor-client. In some exemplary embodiments, each record may be monitored, categorized, and reassigned in a predetermined manner and offered to one or more alternative realtor-clients. As such, upon receipt of a request from a realtor-client for a selected record, the system may register a transaction concerning the lead or scheduled appointment with the realtor-client's device. As mentioned above, transactions of the leads or scheduled appointments may include offering the records for sale, as well as auctioning of the lead records and scheduled appointment records.

In exemplary embodiments, the system may incorporate an algorithm for matching prospective owners—such as buyers or sellers of real estate—with compatible realtor-clients that match one or more predetermined parameters.

In exemplary embodiments, the system may offer a service provider with a platform suitable for data mining or data aggregation capabilities to continuously extrapolate transactional opportunities such as leads from realtor-clients, which may be monitored and offered back to other realtor-clients of the system.

In exemplary embodiments, the system may incorporate an incentive-based algorithm to help improve each realtor-client's success and maximize each transactional opportunity.

In exemplary embodiments, the system may incorporate an exchange platform, which enables affiliates or third-party participants to introduce offers concerning their own lead records to the realtor-clients of the system.

The following figures illustrate several exemplary embodiments of a system and user interface in accordance with the present invention, as well as several methods, processes or algorithms that may be implemented by such system.

FIG. 1(a) illustrates an entity relationship diagram of a system and business model that may be practiced in accordance with the present invention. More specifically, FIG. 1(a) depicts an entity relationship diagram for system 100, wherein the entities, for which data may be stored and managed, include owners 1, real property 2, leads 3, lead tier protocols 4, sources 5, offers 6, realtor-clients 7, roles 8, transaction protocols 9, social media 10, and agent specialty 11.

A system and business model that may be practiced in accordance with the present invention, includes a membership-based business model that provides users access to different quantities and or types of offers concerning transactional opportunities in real estate. In exemplary embodiments, different memberships may offer users of the system different access privileges to the offers provided. The offers typically involve owners of real property that are presently or have been in the past, interested in consummating a real estate transaction. The offers are generated from a lead depository, which is supplied and replenished from one or more sources that may be integral or affiliated with the service provider. More importantly, the business model implements a set of unique lead management protocols for managing each lead and generating different types of offers including pre-arranged scheduled appointments.

Accordingly, owners 1 may be individuals or entities owning real property that they wish to sell, or entities that are interested in purchasing, or even leasing, real property; properties 2 may be one or more physical locations that are owned by the one or more owners 1 and can be, or have been in the past, the subject of a lead. Leads 3 may include one or more opportunities to list one or more of the properties 2 with a realtor.

Lead tier protocols 4 may include one or more protocols for managing different caliber leads, in order to maximize transacting opportunities. Lead tier 4 protocols may dictate how a lead is categorized and handled at every step of the process—from acquiring the lead, to generating a lead record or a scheduled appointment record from that lead, to generating an offer record that is provided to one or more realtor-clients of system 100. For example, and as will be described in more detail below, these protocols may dictate: the duration of an offer record concerning a lead record or scheduled appointment record; the price at which each lead record or scheduled appointment record may be offered; which realtor-clients will have access to a particular offer record; and where within the system the offer record will be listed.

Sources 5 may include individuals or entities that help generate leads 3. Sources 5 may include lead generation efforts internal to the service provider, or may include external efforts from listing agencies or other affiliates (or even other realtor-clients of system 100) that provide leads to system 100. In exemplary embodiments, sources 5 may implement revenue share tracking methods for tracking which sources have provided the most profitable leads.

Offers 6 are offers for the lead records or scheduled appointment records generated from leads 3, which may be offered either directly to one or more realtor-clients, or to all realtor-clients in a region. Offers 6 may include time-sensitive offers and other attributes dictated by the protocols of lead tier protocols 4, such as timing and pricing. As will be discussed in detail below, a lead may be offered multiple times, even simultaneously and to multiple realtor-clients.

Realtor-clients 7 are the users of system 100. These users of system 100 are typically although not necessarily registered users. In exemplary embodiments, realtor-clients' access to offer records may be governed by assigned roles such as subscriptions to the services provided by the service provider. For example, and without limiting the scope of the invention, the service provider may offer one or more membership categories or levels that define different access privileges to varying types of offer records.

Roles 8 may include the roles, access or permissions allotted to realtor-clients 7 of system 100. Accordingly, roles 8 may be defined by a role-based access control model that dictates the types and or quantities of offers accessible to each realtor-client. In some embodiments, such role-based access control model may be implemented by introducing a membership scheme. For example, and without limiting the scope of the present invention, a realtor-client may choose from one or more membership types, levels, or categories that will grant that realtor-client access to different types of offers for lead records, scheduled appointment records, or other transactional opportunities during a predetermined membership period.

In some embodiments, membership may dictate a predetermined period of time during which to receive and or accept a certain number of offer records. In other embodiments, membership may dictate the types of offer records a realtor-client is allowed to access, purchase, or bid on. In yet other embodiments, membership may dictate how a realtor-client is provided access to these offers—for example, a realtor-client with access privileges under a first membership class may receive notifications directly and exclusively to their mobile device, while realtor-clients with access privileges under a second membership class may only access offers provided via a list of available lead records offered to multiple realtor-clients at the same time. Naturally, different variations may be implemented without deviating from the scope of the present invention. Accordingly, a membership scheme may be one basis for determining one of the roles 8 assigned to each of realtor-clients 7 of system 100.

Transaction protocols 9 may include any transaction method or medium by which realtor-clients 7 may purchase, bid, or otherwise transact in the offer records for leads, scheduled appointments, or transactional opportunities that system 100 offers.

Social media 10 may include the addresses, links, subscriptions, or social media services to which realtor-clients 7 may subscribe to and utilize. This information may be useful for enabling various functions and tools for realtor-clients to manage posts, newsfeeds, and other social media tools within system 100.

Agent Specialties 11 may include the various specialties of realtor-clients 7, such as: buyer's agent, listing agent, foreclosures, short-sales, property management, townhouses, condos, haunted houses, or any other number of specialties that may describe the particular focus of a realtor-client. This information may be useful for targeting offers to those realtor-clients that will be better suited for a particular situation. For example, in some embodiments, offers comprising lead records or scheduled appointment records concerning a foreclosure may be provided to a realtor-client that specializes in foreclosures.

Implementing system 100 will enable the management of leads received, generate quality offer records—concerning lead records or scheduled appointment records based on those leads—and enable management of the records by implementing a set of one or more protocols for determining how long an offer is listed, what price an offer may be offered for and to whom, and where within the system the offer will be listed.

Figure 1B:
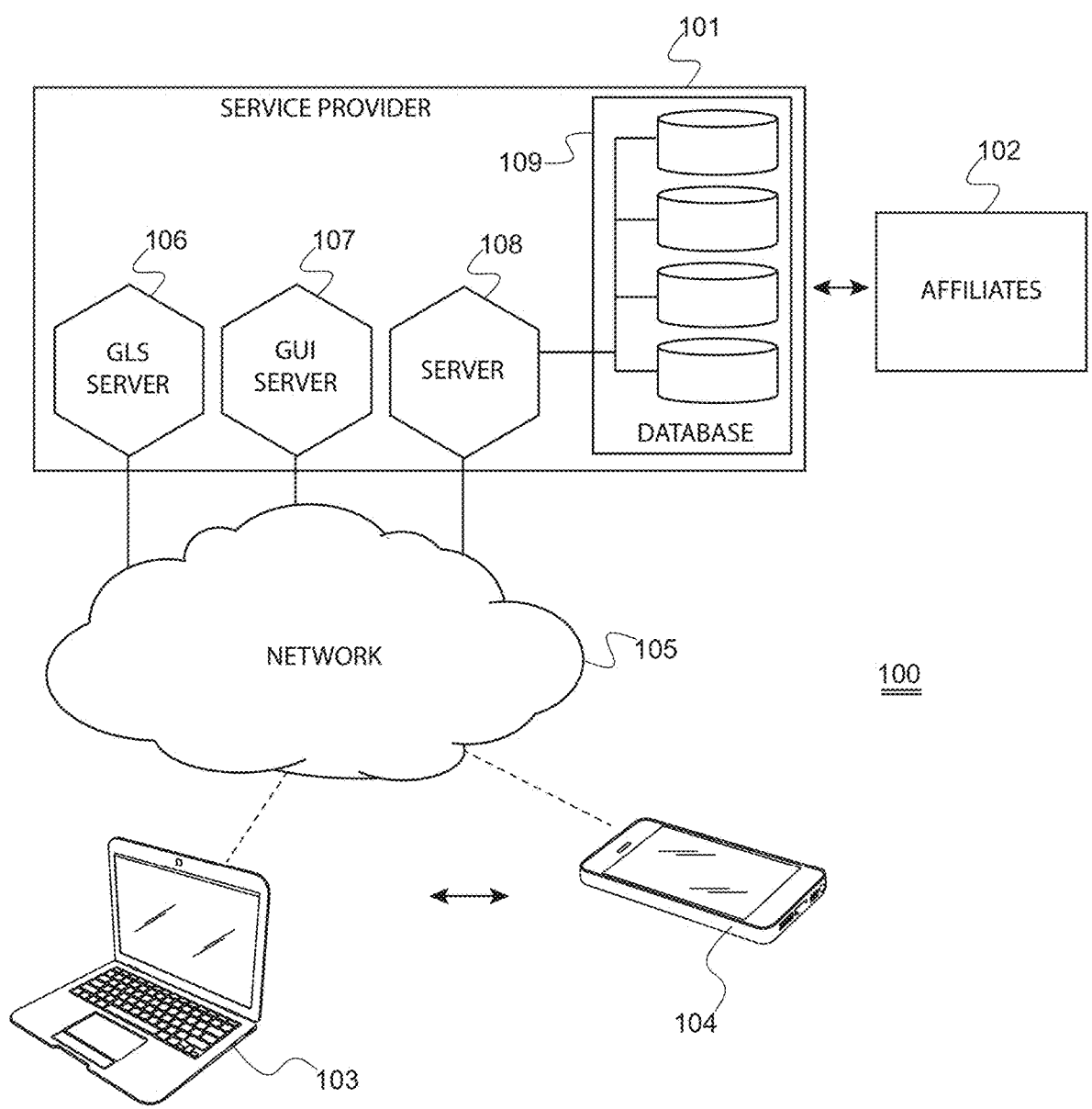
FIG. 1(b) illustrates a system in accordance with one embodiment of the present invention.

Turning to the next figure, FIG. 1(b) illustrates the components of system 100 in accordance with one exemplary embodiment. Generally, system 100 comprises of service provider 101, affiliates 102, and client devices 103 and 104, which communicate with one or more servers (106-108) via network 105, such as the Internet. A database 109 or several databases may be accessible to the one or more servers and implemented in order to store user information, lead information, lead records and scheduled appointment records, service areas or geographic region information, owner information, real property information, and other information that may be relevant to service provider 101.

Service provider 101 may obtain leads or lead information from sources such as affiliates 102, which may include without limitation, third party affiliates or any other suitable resources for obtaining leads, including any internal or external data mining resources that may be available to service provider 101. For example, affiliates 102 may comprise one or more parties that make up sources 5. Typically, service provider 101 may distribute a user interface such as a graphical user interface (GUI) to client devices 103 and 104 via a downloadable mobile application or even a web GUI such as a website.

One or more servers may manage several aspects of system 100. For example, and without deviating from the scope of the present invention, a GUI server 106 may be dedicated to services such as web GUI services or mobile application services. A geographic location services server or GLS server 107 may be implemented for providing geographic location services. For example, GLS server 107 may facilitate identifying lead records or scheduled appointment records associated with real property located within a geographic region relevant to a realtor-client. A process server or main server 108 may be implemented to handle the various requests for information, as well as overseeing transactions of the scheduled appointment records that are purchased, auctioned, or otherwise transacted in system 100. Naturally, system 100 may be configured to perform its tasks with multiple servers or a single server without deviating from the scope of the present invention.

Figure 2A:
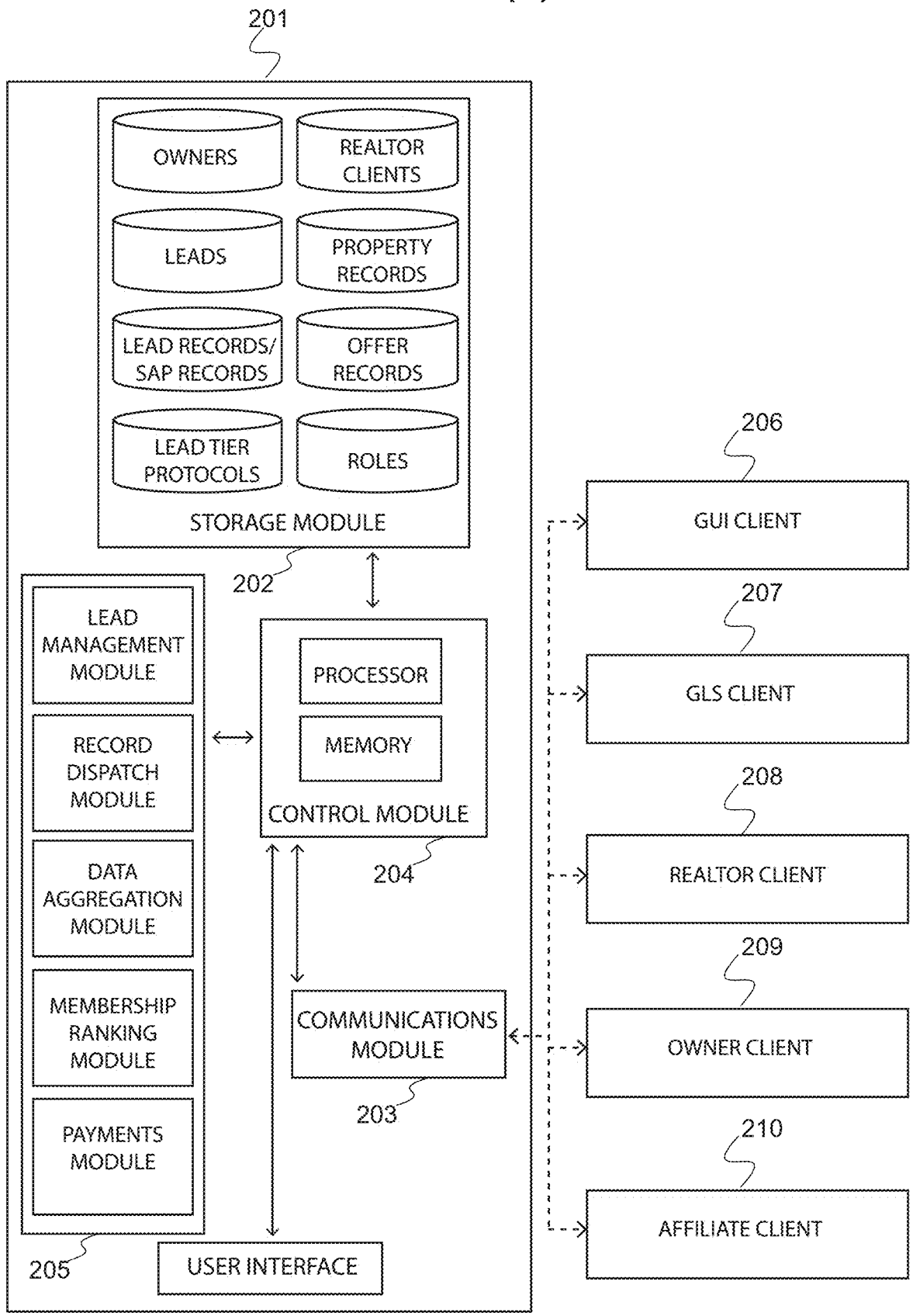
FIG. 2(a) illustrates a computer-readable medium for transacting scheduled appointment records and lead records via a user interface made available to a plurality of client devices, in accordance with one embodiment of the present invention.

FIG. 2(a) illustrates a computer-readable medium for transacting lead records or scheduled appointment records via a user interface made available to a plurality of client devices, in accordance with one embodiment of the present invention. More specifically, FIG. 2(a) illustrates a block diagram of server 201, which includes storage module 202, communications module 203, control module 204 and software module 205. Moreover, server 201 includes GUI client 206, GLS client 207, realtor client 208, owner client 209, and affiliate client 210.

In an exemplary embodiment, server 201 may comprise a two tier server setup with one database layer and one application (web server) layer. This may allow the system to scale user wise by load balancing the application layer and also provide increased security. A cloud based system may run on servers in the Amazon Virtual Private Cloud environment. All physical documents as well as database backups may be encrypted and stored in Amazon's Simple Storage Service (S3). For disaster recovery purposes the system may implement a backup of all current layer images stored in S3 and backups of the database performed incrementally every X minutes and full daily backups. For high availability (and also disaster recovery) purposes based on the service provider's requirements, the system may address failover clustering the database server as well. All security and firewalls may be configured using best practices and industry standard methods. Access to servers may be limited and monitored. All system access attempts (success or failure) may be logged in the database and physical log files as well as access to any base entities.

In other embodiments, server 201 may be a distributed server system set up for robustness in case one server fails. In such exemplary embodiment, server 201 is a World Wide Web (WWW) server connected to the internet. Server 201 may comprise representational state transfer (REST) architecture. Although other architectures may be implemented, a REST server may be desirable to maximize efficiency, particularly in systems that may experience an increasing amount of requests. Furthermore, similar architectures may provide a centralized means of connecting with other system components such as third-party applications or websites that may provide services including websites or mobile device applications and geographic location services. Server 201 may comprise of a plurality of distributed servers configured for fault tolerance, duplication and backup capabilities.

Naturally, server 201 may be configured with any known techniques and in any known manner to achieve a desired security and functionality. Whatever architecture, technique or manner in which server 201 is implemented, server 201 is typically configured to: receive qualified lead information concerning one or more real estate transaction opportunities; generate a lead record and or a scheduled appointment record from the qualified lead information; generate an offer including the lead record and or scheduled appointment record; provide the offer to a client device; and register a transaction concerning the offer with the client device.

In some embodiments, a GLS client may facilitate server 201 with implementing geographic location services. For example, and without limiting the scope of the present invention, server 201 may be further configured to match a geographic location relevant to a realtor-client with the geographic location associated with the scheduled appointment record, in order to provide that realtor-client only with offer records situated in a particular geographic region, which the realtor-client may have previously selected. In alternative embodiments, server 201 may be further configured to match a geographic location of a client device with the geographic location associated with the offer record in order to display on a client device only the scheduled appointments in the vicinity of that device. As may be appreciated, different variations of location-based services may be incorporated without deviating from the scope of the present invention.

Storage module 202 may be coupled either externally or internally to server 201. For example, storage 202 may be one or more long term memory storage devices, such as a hard drive, disk drive, tape unit, Network Attached Storage (NAS) device, Storage Attached Network (SAN) device, RAID disk array, or optical disk array. Although typically a long term memory storage device, storage 202 may be any other memory device without departing from the scope of the present invention. In an exemplary embodiment, storage 202 is striped across redundant storage containers or RAID disk array in a SAN environment for increased data access speeds and robustness. Of course, any other storage configuration would not deviate from the scope of the present invention so long as storage 202 is suitable for the needs of server 202. In one exemplary embodiment, storage module 202 is a cloud-based storage solution suitable to host one or more databases for the system managed by server 201.

Storage module 202 may hold multiple databases containing data objects within data repositories collected by server 201. The databases of storage module 202 may be created by a known database manager using known technologies such as relational architecture and SQL access, such as Microsoft™ SQL or Oracle™ DB. However, the database of storage module 202 may be as simple as a series of files stored in a directory, with a text file listing filename locations without departing from the scope of the present invention. In one embodiment, the one or more databases of storage module 202 may be a combination of a known database manager, and an organized directory tree structure, wherein the database manager stores text information in the database itself, but stores multimedia information and other non-text information as filename locations of files stored in an organized directory tree structure.

In an embodiment wherein server 201 relies on cloud computing, storage module 202 may include technologies offered by Amazon™ such as Amazon™ Elastic Compute Cloud (AWS EC2), whereby storage module 202 may employ MySQL™ and AWS EC2™ instances.

The one or more databases of storage module 202 may hold multiple data repositories corresponding to: owners such as prospective buyers or sellers of real property; real property information; sources or affiliates such as entities that supply the system with leads; lead records and scheduled appointment records that have been generated from leads; relator-clients; the various roles or access privileges that may govern each realtor-client's access to offer records; service areas; offer records; lead tier protocols or rules that govern different aspects of each record; and any other useful information that may be obtained via suitable data mining resources and utilized to continuously generate new leads.

Communications module 203 may be implemented as a single device or multiple devices configured to connect server 201 to a network such as the internet, and or communicate server 201 to other system components, including other servers such as web servers, mobile device application servers, and/or a geographic location services servers.

Control module 204 typically includes one or more processors and memory configured to execute a set of one or more executable instructions such as program code and/or data stored on one or more computer readable mediums to implement the various applications, data, steps described below and any other instructions pertinent to the functions of server 201. For example, such executable instructions may be included in software module 205.

Software module 205 may include one or more modules for the various functions of the system managed by server 201. For example, and without limiting the scope of the present invention, software module 205 may include a lead management module to implement lead tier protocols, a record dispatch module for matching offers to best-suited realtor-clients, a data aggregation module for requesting and gathering information from realtor-clients, a membership ranking module for implementing an incentive-based program for realtor-clients, a payments module for handling payments for the offer records concerning lead records and scheduled appointment records, and other software modules that help create, track and monitor opportunities for realtor-clients of the system.

Moreover, software module 205 is typically configured to facilitate customer relationship management (CRM) functions and reporting. For example, and without deviating from the scope of the present invention, once a realtor-client selects and purchases an offer record, the lead record or scheduled appointment record associated with the offer record may be stored in a history or prospects tab ultimately to make its way to a reporting tool that allows for the realtor-client to manage his or her leads.

Moreover, software module 205 is typically configured to facilitate sending requests for information between realtors. For example, and without deviating from the scope of the present invention, realtors may be able to post a questions and receive answers on a live platform.

Server 201 may include various clients, such GUI client 206, GLS client 207, realtor client 208, owner client 209, and affiliate client 210. These clients may include hardware components and software components configured to communicate with server 201 in order to receive requests from client devices, use location-based methods to provide relevant records, handle the various requests for information, as well as overseeing transactions of the leads or scheduled appointment records that are purchased, auctioned, or otherwise transacted in the system via server 201.

Turning now to FIG. 2(b), several exemplary embodiments of data structures utilized by a system in accordance with the present invention are illustrated. More specifically, FIG. 2(b) exemplarily illustrates embodiments of data structures for a lead record, a scheduled appointment record, and an offer record—such as lead record 211, scheduled appointment record 212, offer record 213, and offer record 214.

A lead record in accordance with the present invention typically includes pertinent information concerning a lead that has been received by system 100 via affiliates 102 or a similar lead exchange platform. Lead record 211 may include a lead ID 221 for identifying and keeping track of lead record 211; a property ID 222 for identifying or referencing real property that is the subject of a lead; an owner ID 223 for identifying an owner (for example a seller that is interested in selling a property associated with the property ID); source ID 224 for identifying a source of the lead information; a CRM ID 225 for aggregate reporting purposes; lead type 226 indicator for identifying the type of lead—such as a lead for a potential sale or a lead for a potential buy; lead tier 227 for indicating a lead category according to a protocol for managing lead records and scheduled appointment records; lead price 228 for designating a predetermined price for the record; dispatch information 229 concerning comments or useful information that may help sell the lead; and lead status 230 may provide an indicator for keeping track of whether lead record 211 is active, has been sold, or is no longer available for generating an offer record.

Lead record 211 refers to and may be generated from various information and other records stored in the one or more databases of system 100. For example, and without limiting the scope of the present invention, property ID 222 may refer to a property record (stored in one or more databases of system 100) of a particular property including the property address, the property type, a square-footage, number of bedrooms, number of bathrooms, and lot size. Owner ID 223 may refer to an owner record (stored in one or more databases of system 100) of an individual or entity including the owner's name and last name, or entity name, address, phone number, and email address. Source ID 224 may refer to a source record (stored in one or more databases of system 100) of a lead source including the source's individual or entity name, lead cost (i.e. cost at which the lead information may have been purchased from the lead source, or even a lead rate indicative of a percentage commission that may be supplied to the lead source in the event the lead record is offered and sold). Lead type 226 may designate a lead type indicative of the type of transaction sought by an interested party (e.g. owner ID 223) such as a lead for a potential purchase or a lead for a potential sale of the property identified by property ID 222. Lead tier 227 may refer to a lead category as may be defined by lead tier protocols and may dictate the timing, pricing, and means in which an offer record based on lead record 211 may be offered to one or more realtor-clients. Lead price 228 may be a suggested or predetermined price for lead record 211 and as will be discussed below may be adjusted or updated in accordance with lead tier 227 or the category assigned to lead record 211 prior to being offered. Dispatch information 229 may be generated at the time lead record 211 is created or may be extracted from the lead or qualified lead concerning the owner or property associated with lead record 211. For example, dispatch information 229 may comprise pertinent information such as an urgency to sell due to a divorce, personal information such as a preferred language spoken by the owner, or any other pertinent information that may be useful to a realtor-client; this information may be included in an offer record associated with lead record 211.

Scheduled appointment record 212 is similar to lead record 211. Moreover, scheduled appointment records may be a type of lead record offered by the system whereby an actual date, time and place for a live meeting has been confirmed by an interested party. As such, an exemplary scheduled appointment record 212 may include the same information as lead record 211 with the additional scheduled information 231. This may occur when a lead record is followed-up on by a service provider administrator or agent for the service provider. For example, an agent of the service provider may contact an owner identified by lead record 211 and confirmed that a specific date, time and place for a meeting with a realtor is desired. Accordingly, in addition to the information that is included with lead record 211, scheduled appointment record 212 may include said scheduled information 231. Similarly, scheduled appointment record 212 may include a different lead price, such as lead price 228a because the value of the record is typically elevated due to the fact that the opportunity of a specific date, time and place meeting creates a better prospect than when the realtor-client purchases a lead record that will require the realtor-client to advance the prospective transaction on their own. A pre-scheduled meeting carries particular value to a realtor, and as such, scheduled appointment records may be valued different. Of course, other factors may alter a lead value, such as the lead tier and any dispatch information that may increase or decrease the chances of a successful prospective transaction.

Offer records such as offer record 213 may be generated from lead record 211 or scheduled appointment record 212. In the exemplary embodiment shown, offer record 213 is an offer concerning scheduled appointment record 212. Accordingly, offer record 213 may include offer record ID 232, lead ID 221 (to keep track of the lead from which offer record 213 was based), offer type 233, offer timer 234, offer cap 235, agent ID 236, lead tier 227, lead price 228a and scheduled information 231.

Offer type 233 may designate a method in which offer record 213 is provided to one or more realtor-clients. In an exemplary embodiment, offer type 233 may be designated as 'individual' or 'market' which indicates whether the offer will be delivered via system 100 to a single relator-client or a plurality of realtor-clients. For example, offer record 213 may be an offer concerning scheduled appointment record 212, and may have an offer type 233 designating offer record 213 for 'individual' delivery. Accordingly, in this example, offer record 213 may be provided to a single realtor-client, which may have been previously identified based on known parameters including: that realtor-client's role or permissions based on a membership subscription; a geographic region or location of the property associated with property ID 222, a specialty of the realtor-client listed in the realtor-client's profile, and any other information or parameters that points towards offer record 213 being a good fit for the targeted realtor-client (i.e. and having a high likelihood that the targeted realtor-client will accept the offer and succeed in consummating the transaction proposed by the interested party). Of course, without limiting the scope of the present invention, other offer types may include several variations on the above, such as an offer type that allows offer record 213 to be delivered to more than one realtor-client simultaneously but not necessarily every realtor-client in the system or 'market' at the same time.

Offer timer 234 may refer to a predetermined time period during which a realtor-client, to whom offer record 213 has been provided, can accept or decline the offer. The predetermined time period may be based on lead tier 227. A timer for an offer such as offer 213 (concerning scheduled appointment record 212) may be desirable because of the time-sensitive nature of a scheduled appointment. Moreover, a timer may provide an incentive to realtor-clients that know this opportunity may be passed on to another realtor-client if the targeted realtor-client declines.

Offer cap 235 may refer to a designation of how many times offer record 213 is offered before there is a cool-down period. For example, offer cap 234 may be set at 5 times. As such, if a first realtor-client is delivered offer record 213 and that first realtor-client does not accept or declines the offer, offer record 213 may be provided to a second matching realtor-client. If, however, offer record 235 has been offered (i.e. delivered) to a fifth realtor-client and declined, offer cap 234 will prevent the system from delivering offer record 235 to a sixth realtor-client. This will allow the system administrators time to re-review and reassess the lead or qualified lead information, as well as review any feedback from the realtor-clients declining the offer record; for example, there may be some factors that realtors are aware of concerning the property associated with property ID 223, or any other number of factors that the service provider is unaware of but may learn from such feedback. Moreover, during a predetermined cooldown period, agents for the service provider may decide to amend lead price 228a, re-categorize or re-assign lead tier 227, or generate a new offer record altogether.

Agent ID 236 may refer to a realtor record (stored in one or more databases of system 100) of an individual or entity associated with a realtor-client including the realtor's name and last name, or entity name, realtor's license number, address, phone number, email address, specialty or professional profile, contact preferences, and role (i.e. membership and subscription status). Typically, agent ID 236 is an identification associated with the realtor-client to whom offer 213 is delivered. In some circumstances, agent ID 236 may include more than one ID if offer record 213 is delivered to a plurality of realtor-clients. In other embodiments, agent ID may not be part of an offer record, for example if the offer record is designated 'market' and targeted to all realtor-clients in a particular region. In yet other embodiments, the offer record may include a role identifier such as role ID 243 that indicates which realtor-clients of system 100 are eligible to receive or have access to a particular offer record.

Offer information 237 may be information generated or extrapolated from dispatch information 229. Typically, this offer information 237 may provide key facts or desirable attributes about lead record 211 or (in this case) scheduled appointment record 212, which may be attractive to the realtor-client associated with agent ID 236. Other than being informative, offer information 237 may also serve as a marketing means to garner interest in offer record 213 and heighten the likelihood that offer record 213 will be accepted (whether by purchase or bid) by the realtor-client associated with agent ID 236 or with access to offer record 213 per role ID 243.

Offer record 214 is a similar offer record to offer record 213, but one based on a lead record, thus not including scheduling information such as scheduled information 231. Further, offer record 214 does not include agent ID 236 but role ID 243 associated with a role designation that may dictate to which realtor-clients offer record 214 may be delivered, or which realtor-clients of system 100 may even have access to offer record 214. Because offer record 214 is exemplarily generated from a different lead record than lead record 211, offer record 214 will have a different lead ID 239, and may have a different offer type 240, offer timer 241, offer cap 242, lead tier 244, and lead price 245—depending on the type and quality of the lead information that is associated with the lead record being offered through offer 214. Similarly, offer information 246 will be typically tailored to the particular facts of the lead information on which offer 214 is based, or in some embodiments, offer information 246 may also comprise a predetermined message based on role ID 243, offer type 240, lead tier 244, lead price 245, or any combination thereof.

Of course, other variations of lead records, scheduled appointment records, and offer records may be possible and organized and structured with more or less data without deviating from the scope of the present invention.

Turning to the next several figures, methods in accordance with the present invention are discussed in turn.

Figure 3:
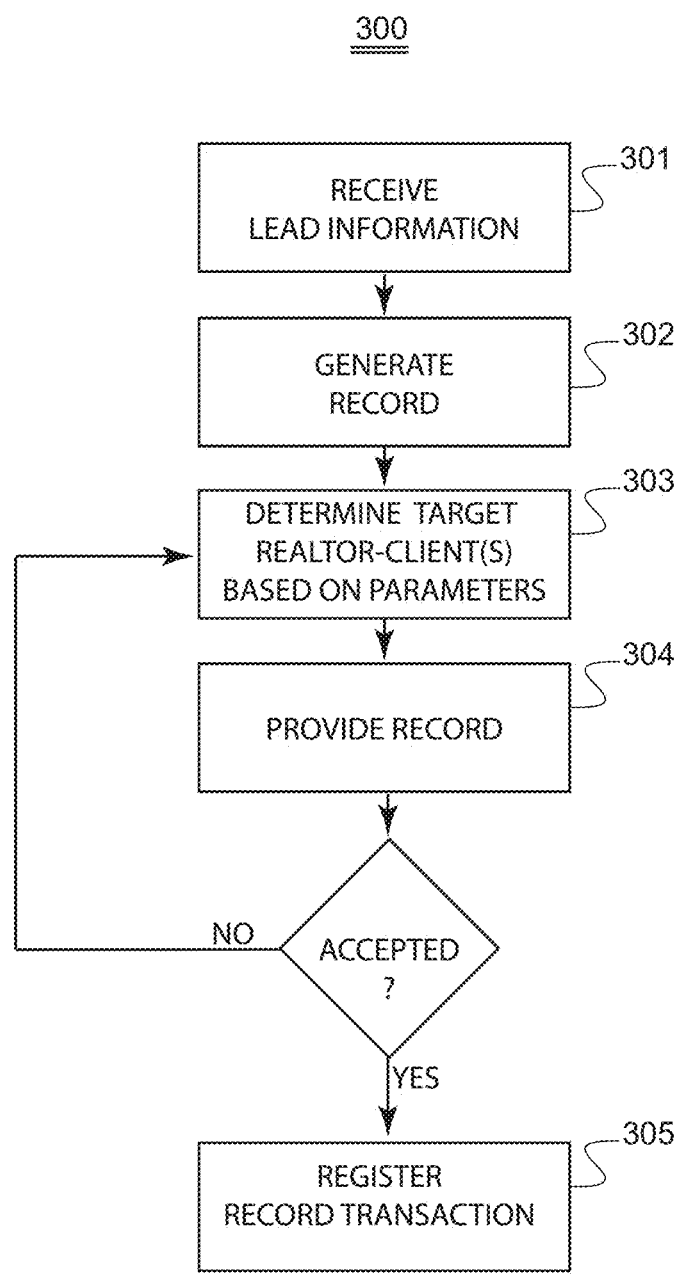
FIG. 3 illustrates a flowchart depicting method 300 for transacting a lead record or scheduled appointment record, in accordance with practice of one embodiment of the present invention.

FIG. 3 illustrates a flowchart depicting method 300 for transacting a lead record or scheduled appointment record, in accordance with practice of one embodiment of the present invention. Although method 300 is shown in a particular sequence of steps, other conceivable sequence of the steps may be practiced without deviating from the scope of the present invention. In an exemplary embodiment, method 300 comprises: receiving qualified lead information concerning one or more real estate transaction opportunities (301); generating a record, such as a lead record or a scheduled appointment record from the qualified lead information (302); determining one or more target realtor-clients based on a set of one or more parameters (303); providing the lead or scheduled appointment record to a client device associated with the one or more targeted realtor-clients (304); and registering a transaction with the client device concerning the scheduled appointment record (305).

In step 301 a lead received from a source such as affiliates 102 may be checked for accuracy, quality, and thus qualified as a qualified lead. Information pertinent to the lead or qualified lead may be confirmed and entered into a database of the system to create a qualified lead record. This record may include information pertaining to the identity of an owner of real property or an entity interested in a particular property, the geographic location or address of the real property, and the nature of the entity's interest in the real property with respect to the kind of transactional opportunity sought—i.e. purchase, sale, or lease. As such, in exemplary embodiments, qualified lead information concerning one or more real estate transaction opportunities may be received and stored. For example, step 301 may encompass receiving the information by an agent of the service provider and inputting the information in one or more databases of system 100. Information pertaining to an interested party such as an owner of a property may be received and stored in a depository of owners and assigned an owner ID. Similarly, property information pertaining to the subject matter property of the lead may be stored in a property depository of system 100 and assigned a property ID. Other information provided with the lead may be aggregated into the one or more databases of system 100, including information that will be attractive to potential realtor-clients to which an offer record may be delivered.

In step 302 a record may be generated from the lead information in the one or more databases of system 100. For example, and without limiting the scope of the present invention, once qualified lead information has been confirmed and entered into the system, an agent of the service provider may contact the interested party (e.g. owner of real estate seeking to sell) in order to confirm a specific date, time and place for an appointment with a realtor for pursuing a real estate transaction.

Additionally, in exemplary embodiments, the qualified lead information may be tagged, flagged, or otherwise marked with additional information that will be helpful to a realtor. Such information may include profile information pertaining to the owner/interested party such as sex, race, religion, marriage status, family size, etc. For example, a scheduled appointment record may include information pointing out that an owner that has recently divorced is seeking to sell their current home. Other examples of additional information may include, without limitation, an indication pertinent to a level of interest or urgency. This information may be useful not only for the realtor that ultimately accepts and purchases or successfully bids on the offer associated with the qualified lead, but also to the service provider—for this information may aid valuation of the qualified lead information, and ultimately the scheduled appointment record generated therefrom.

Similarly, a lead record—rather than a scheduled appointment record may be generated from the lead information. In an exemplary embodiment, a lead record may be autonomously generated by one or more software modules that sift through the various depositories and gather related information to generate a lead record such as lead record 211. In some embodiments, an agent of the service provider may manually enter scheduling information to a lead record in order to generate a scheduled appointment record such as scheduled appointment record 212. In other embodiments, an interested party or owner may have already provided a preferred time and date for a scheduled appointment and the system may automatically generate a scheduled appointment record such as scheduled appointment record 212.

Accordingly, in step 302, a lead record or a scheduled appointment record that includes the qualified lead information may be generated, stored, and prepared for offer via the user interface or GUI provided to users of system 100. Moreover, in exemplary embodiments, an offer record such as offer records 213 and 214 may be generated from lead records and scheduled appointment records in order to deliver offers concerning leads or scheduled appointments to the realtor-clients of system 100. Offer records are desirable because they contain limited information that allow the service provider to track, monitor, and monetize the information without having to provide the information included in each lead record or scheduled appointment record such as the name of the owner, or property information associated with the lead information.

In step 303, a determination may be made concerning one or more target realtor-clients to whom to offer the offer record. This determination may be based on a wide range of parameters including but not limited to: geographic region of the real property; geographic region of one or more users; role or membership status of one or more realtor-clients; role or membership class of one or more realtor-clients; profile information of the interested party or owner associated with the offer record; profile information associated with one or more realtor-clients; and any other parameters that can be useful in determining the best set of one or more realtor-clients suitable for the offered record.

For example, and without deviating from the scope of the present invention, in distributing a scheduled appointment record, system 100 may select various parameters in order to reach the most eligible realtor-clients that may be interested in the scheduled appointment record, and or will be most likely successful in consummating the anticipated transaction associated with the record. One such parameter may include a geographic region in which the real property or scheduled meeting associated with the record is located. As such, scheduled appointment records may be offered for purchase or bidding to one or more users that have indicated an interest in the particular geographical region.

Similarly, another parameter may include a predetermined role or membership status or membership class of relator-clients—this may include determining which realtor-clients may be eligible to receive an offer concerning the scheduled appointment record. For example, practice of some embodiments of the present invention may include implementation of membership schemes that allow certain members priority or even exclusive access to certain types of lead records or scheduled appointment records. As such, a relator-client's membership may be a parameter that the system utilizes in determining whether to extend (i.e. deliver) the offer record to a client device of one or more realtor-clients.

Similarly, another parameter or sets of parameters may include profile information pertaining to the interested party (e.g. owner of real estate interested in selling) and profile information of one or more realtor-clients of system 100. This information may be used to match compatible personalities, similar backgrounds or spoken language, or even match an interested party with a realtor-client that specializes in particular situations (e.g. foreclosures). As profile information can tell the service provider useful information about the parties involved, this information may be used to determine a match that is most likely to succeed in consummating a transactional opportunity. Additionally, as will be discussed further below, the service provider may use feedback from a relator-clients' experience to better aid matching that realtor-client with future opportunities.

Accordingly, in step 303, a determination may be made concerning one or more target realtor-clients for offering the record—this determination based on one or more parameters.

In step 304, the offer record may be provided via a GUI or mobile app to one or more targeted relator-clients. In exemplary embodiments, an offer record concerning a lead record or a scheduled appointment record may be provided via an alert or notification delivered to a client device. Such alert or notification may launch a mobile application to deliver an offer for the scheduled appointment record—including an option for the realtor-client to sell or bid on the offer record. Moreover, in exemplary embodiments (see FIG. 5, FIG. 9, FIG. 14 below) a predetermined time limit may be provided with each offer, during which a relator-client must select to either purchase or make a bid for the lead or scheduled appointment.

In step 305, where the offer record is accepted by a relator-client of system 100, payment is received via a suitable transaction means (i.e. typically via the GUI vehicle in which the offer record is provided) and registered by the system. Acceptance may include a successful bid amongst several users or a purchase of the offer record. As mentioned above, depending on the business model implemented, a relator-client that accepts a scheduled appointment record may either: purchase each record at the time of the acceptance of the offer, or may have—per a prior membership agreement—pre-purchased a predetermined number of records for a predetermined period of time. In the former case, well known technologies may be implemented to receive payment information via a suitable transaction module and the payment may be registered by system 100; alternatively, each relator-client may have payment information associated with their account and proper charges may be deducted accordingly. In the latter case, the system may register the purchase and deduct from any total allotted records per the relator-client's membership agreement. In any event, if an offer record is accepted, the transaction may be registered with the client device.

In the event that an offer record is not accepted by any relator-client originally targeted, a step 303 determination may be re-initiated in order to determine a new set of one or more relator-clients that may be suitable for the specific offer.

Figure 4:
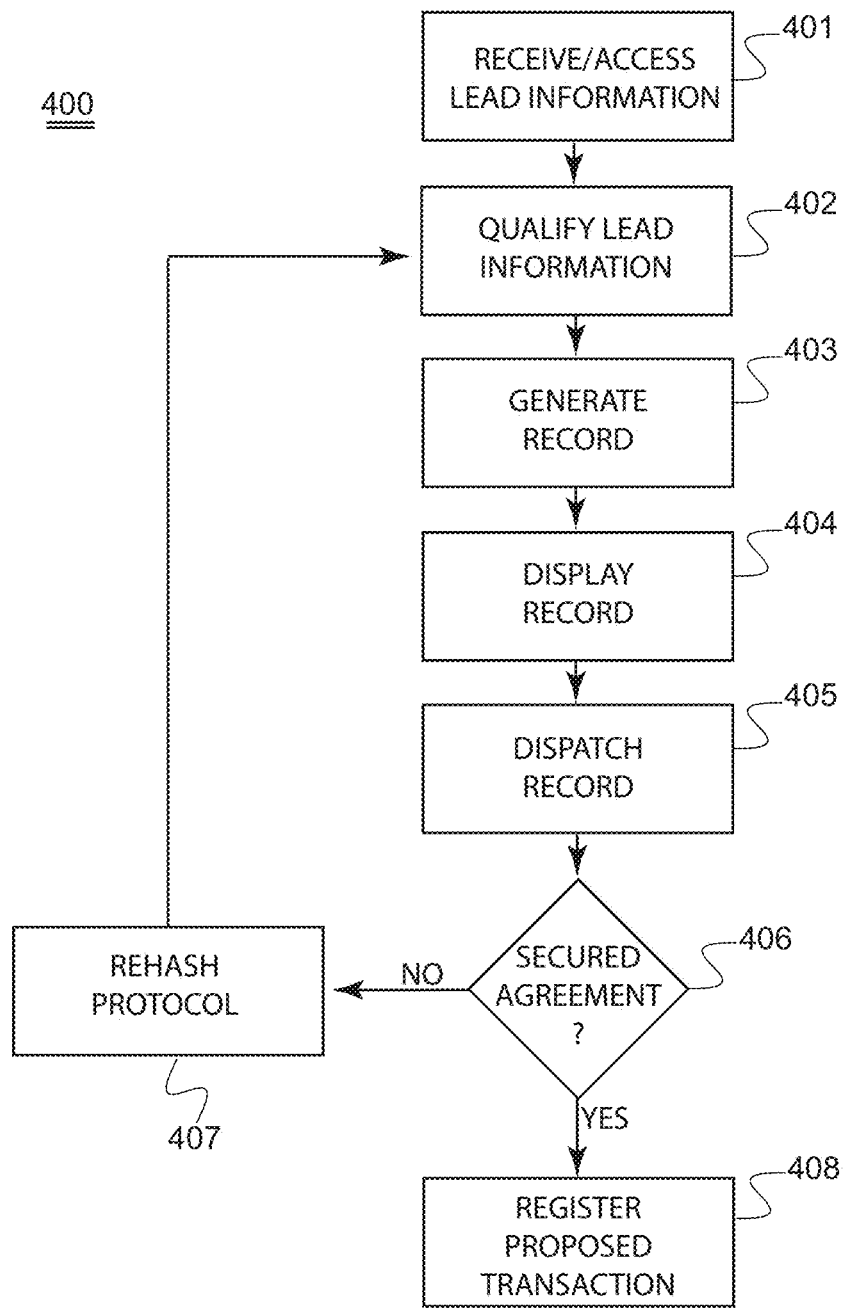
FIG. 4 illustrates a flowchart depicting a method for generating and managing records, in accordance with practice of one embodiment of the present invention.

Turning now to the next figure, FIG. 4. illustrates a flowchart depicting a method for generating and managing records, in accordance with practice of one embodiment of the present invention. Although method 400 is shown in a particular sequence of steps, other conceivable sequence of the steps may be practiced without deviating from the scope of the present invention.

In an exemplary embodiment, method 400 for generating and managing offer records comprises: receiving or accessing lead information (401); qualifying the lead information (402); generating an offer record based on the qualified lead information (403); displaying the offer record on a user interface accessible to the client devices (404); dispatching or assigning an offer record to a realtor-client (405); determining whether an agreement concerning the proposed transaction has been secured (406); and either: rehashing the offer record if an agreement was not secured (407), or registering with the client device the consummation of the proposed transaction (408).

To explain the steps above, the first steps 401-403 are similar to those disclosed with reference to method 300; the latter steps 404-408 focus on managing an offer record associated with a lead record or scheduled appointment record, wherein management of the offer record depends on whether the proposed transaction was consummated by the interested parties with the aid of the realtor to whom the offer record was dispatched.

In step 401, receiving or accessing lead information may include identifying and recording a transaction opportunity from a source such as affiliates 102. As mentioned above, lead information may be received from a variety of channels without deviating from the scope of the present invention. For example, lead information may be obtained from data mining or data aggregation methods, including data aggregation algorithms implemented with the present system, affiliated websites, or purchased lists, or a variety of third-party sources.

In step 402, lead information is qualified, which typically involves confirming that a lead meets all or some of the criteria to be offered to a realtor. Qualification can be automated or via a marketing agent phone call, email, or other live means of corresponding with the interested party.

In step 403, once the service provider connects with the lead and schedules an actual meeting with a time and date, a scheduled appointment record may be generated and entered into the system; an offer record based on the scheduled appointment record may be automatically generated or manually created as discussed above. Alternatively, if a specific scheduled time cannot be obtained, or the lead information does not give rise to a scheduled appointment, a lead record may be generated instead. Whether a lead record or a scheduled appointment record is generated, an offer record may be generated therefrom.

In step 404, the offer record is provided or displayed to one or more realtor-clients via the GUI. In exemplary embodiments (e.g. see FIG. 9, FIG. 10), notifications via a mobile application may be provided to notify a realtor-client of an offer record concerning a lead record or scheduled appointment record is available to that realtor-client. In other exemplary embodiments, an email communication may be sent to a realtor-client. In other embodiments, the offer record is offered along with other offer records to a plurality of realtor-clients with role id's or permissions to access the offer record (see e.g. FIG. 11).

In step 405, the offer record is dispatched to a realtor-client that has either purchased, successfully bid on, or otherwise accepted the offer record to obtain the associated lead record or scheduled appointment record. In exemplary embodiments, this may trigger one or more protocols for: tracking that realtor-client's progress with the lead or scheduled appointment; categorizing the lead record or scheduled appointment record in accordance with a predetermined scheme (e.g. see FIG. 6, FIG. 7); triggering predetermined time periods allotted for the realtor-client to generate a successful transaction; or triggering other calls for action that may aid the realtor-client to a successful consummation of the proposed transaction (e.g. see FIG. 18).

In step 406, determining whether an agreement concerning the proposed transaction has been secured, may include determining that the realtor-client is able to secure a listing agreement involving the interested party or property owner. This may include obtaining feedback from the realtor-client and or confirmation of the transaction by way of input from the realtor-client via the client device.

If a lead follow-up or appointment is unsuccessful, in step 407, a rehash protocol may be initiated whereby the offer record is sent back to a recycling process that allows the service provider to maximize the ability to drive sales by, for example, offering the opportunity to a different set of one or more realtor-clients.

If the lead follow-up or appointment was successful, in step 408, the system may register with the client device that the consummation of the proposed transaction was successful. This step may be desirable because the service provider may have an interest in a predetermined percentage or commission associated with a closing of the proposed transaction.

Figure 5:
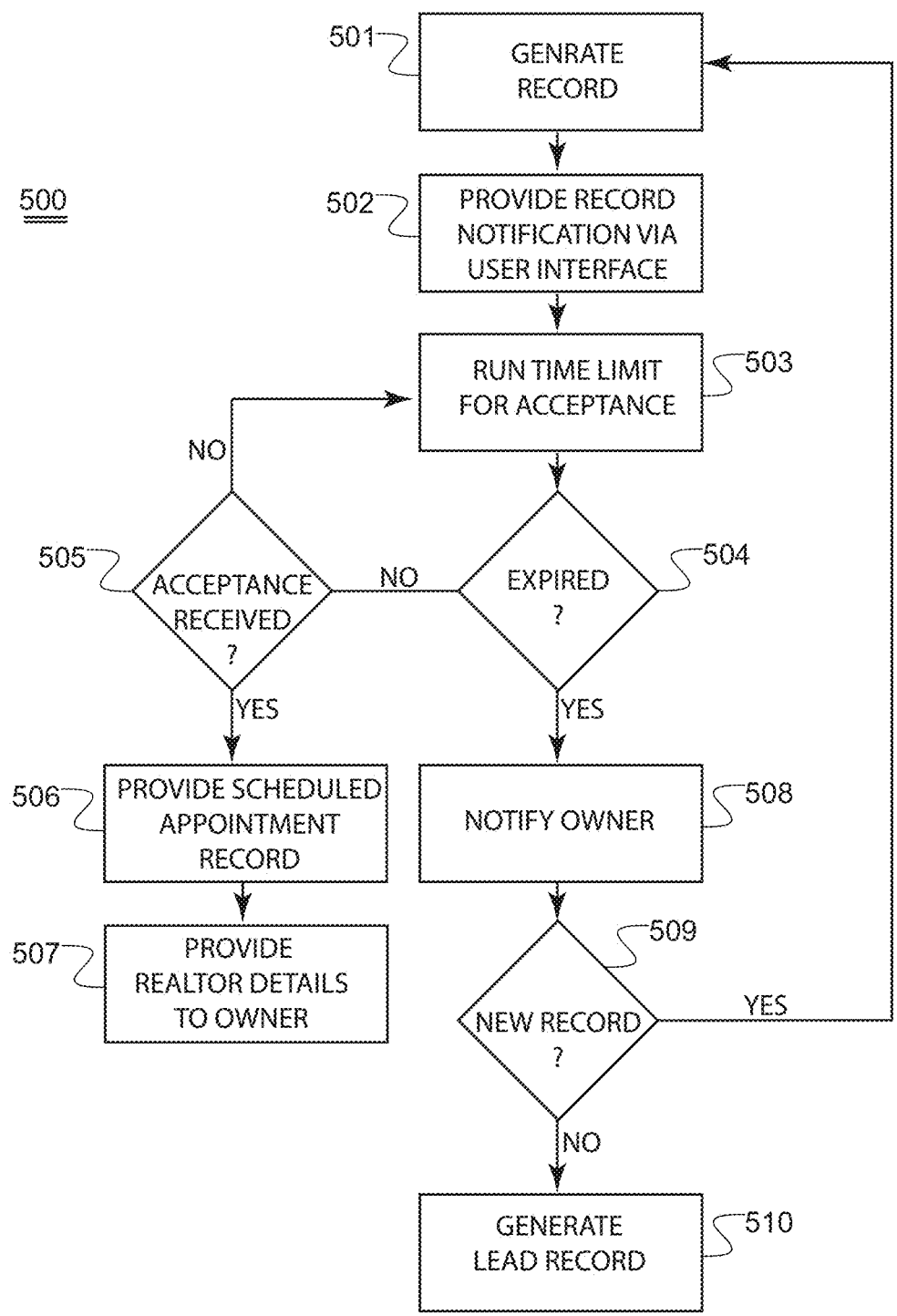
FIG. 5 illustrates a flowchart depicting a method for transacting records in accordance with practice of one embodiment of the present invention.

Turning now to the next figure, FIG. 5 illustrates a flowchart depicting a method for transacting scheduled appointment records in accordance with practice of one embodiment of the present invention. More specifically, method 500 is an exemplary method for providing an offer concerning a scheduled appointment record, which is time-sensitive and thus expires after a predetermined period of time. It is noted that although method 500 is shown in a particular sequence of steps, other conceivable sequence of the steps may be practiced without deviating from the scope of the present invention.

In step 501, a scheduled appointment record may be generated—meaning that a specific date, time, and place for a meeting with an interested party has been scheduled; thus because the interested party expects a meeting to occur, the scheduled appointment must be offered on a limited time basis, which requires a predetermined time period for the offer to expire. Accordingly, in one exemplary embodiment, an offer record concerning a scheduled appointment record may include time limitation information (e.g. offer timer 234) for deriving a duration of an offer record and triggering a time limit or count-down for the realtor-client to accept or decline the offer record.

In step 502, the offer record may be provided to realtor-clients or a single realtor-client—by for example sending a notification of the record to at least one targeted realtor-client that has been matched with the interested party. In exemplary embodiments, an offer record does not include all the information included in the scheduled appointment record or lead record on which the offer record may be based on. For example, even though a lead record may include property information and information concerning the identify of an interested party (see FIG. 2(b) for example), an offer record may omit this information so as to conceal it from realtor-clients prior to their acceptance of the offer record by purchasing or successfully bidding on the offer record.

In step 503, the system may use the time limitation information previously associated with an offer record in order to generate an active time limit on the offer. In exemplary embodiments, this may include providing or displaying on the client device an offer record that includes a timer. In such embodiments (e.g. see FIG. 14) a notification may be sent to a realtor-client via client device, which includes a count-down clock. In other exemplary embodiments, a notification alerts a realtor-client to launch a mobile device application in which the offer record including a time limitation or timer is displayed.

Figure 13:
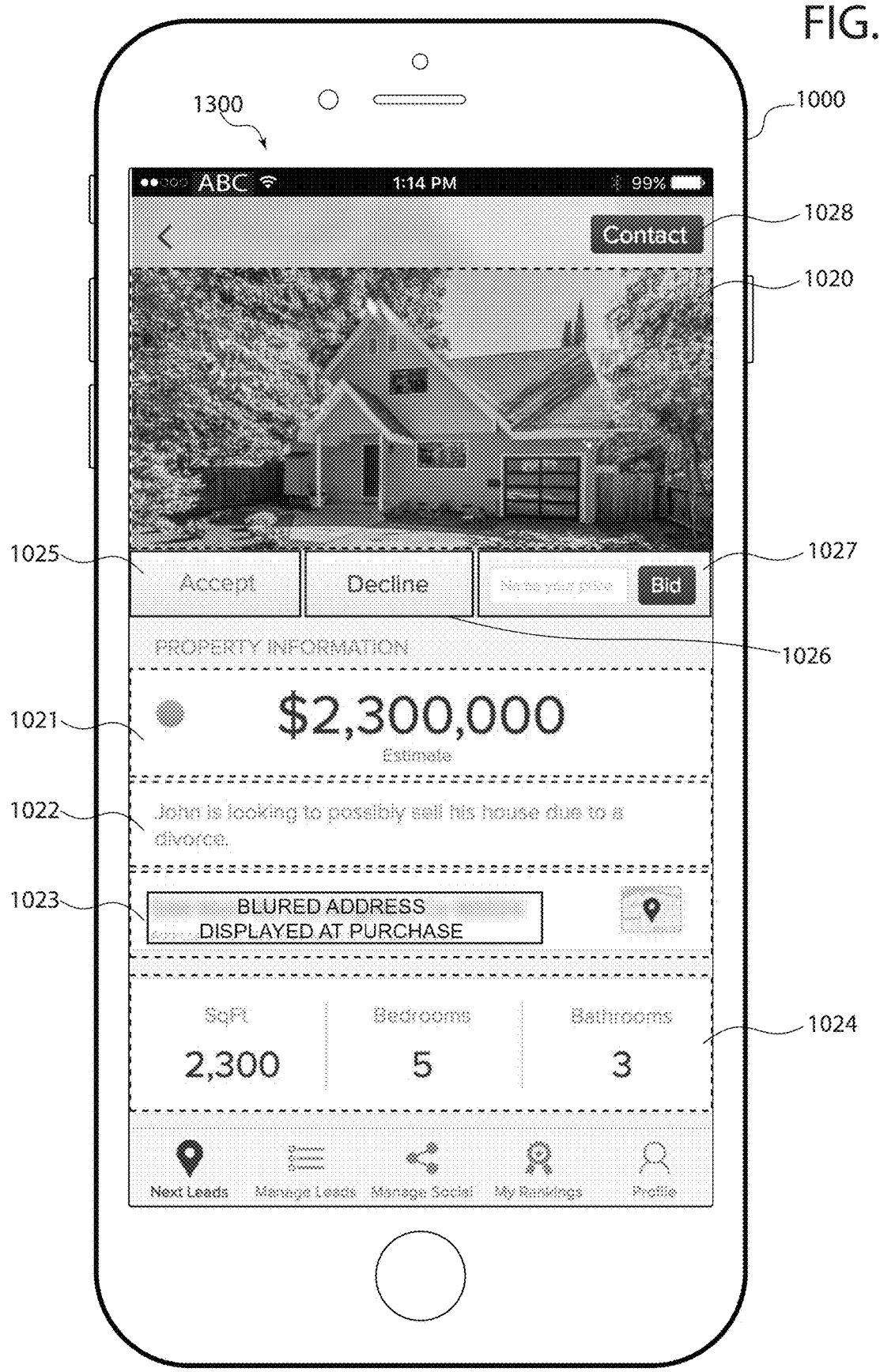
FIG. 13 illustrates an exemplary user interface configured to facilitate the transaction of scheduled appointment records, in accordance with one embodiment of the present invention.
Figure 14:
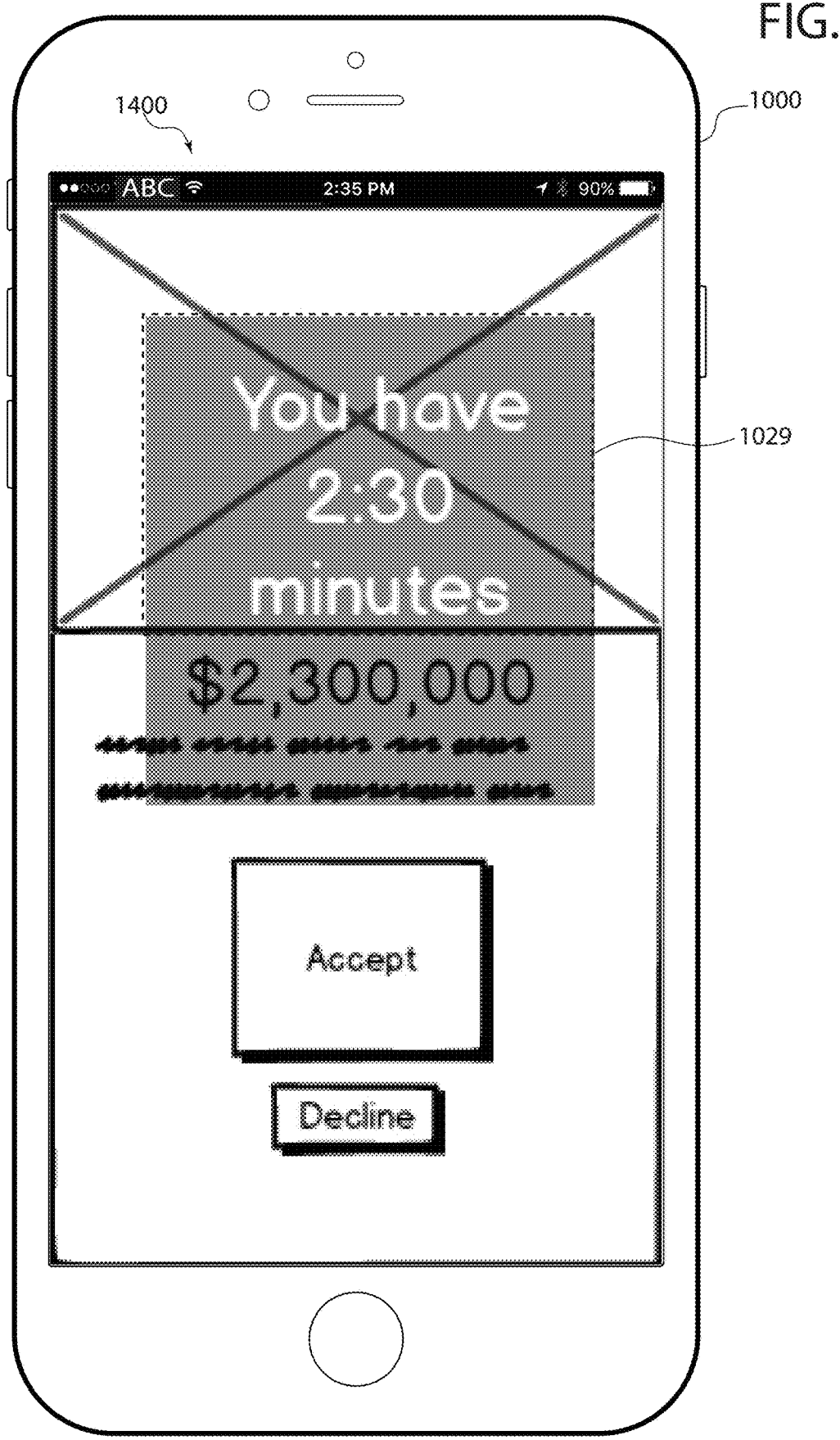
FIG. 14 illustrates an exemplary interface for providing a time-sensitive offer to purchase a scheduled appointment record.

As mentioned above, only minimum information is provided in an offer record. For example, and without limiting the scope of the present invention, an offer record concerning a scheduled appointment record may include a general description of the real property, some minor facts that may be useful to a potential realtor (i.e. price range, vicinity, etc.) but not include specific information such as contact information for the interested party, the interested party's name, or the address of the real property at play, or other more pertinent information that may be available through the lead record or scheduled appointment record. FIG. 13 and FIG. 14 illustrate two possible user interfaces that allow realtor-clients to view an offer record concerning a scheduled appointment record in order to purchase or bid on.

In steps 504 and 505 determinations may be made depending on whether the allotted time period has expired and or the offer has been accepted.

In step 506, if at least one realtor-client has accepted an offer record concerning the scheduled appointment record, the scheduled appointment record is provided to the realtor-client—meaning that all pertinent information is made accessible to the realtor-client, including contact information or a contact means to contact the interested party or owner, the specific property ID and address associated with the scheduled appointment record, the scheduled date, time and place for the scheduled appointment, and any additional specifics pertaining to the scheduled appointment record.

In step 507, upon confirmation that an offer has been accepted and a scheduled appointment record was provided to a realtor-client, the interested party or owner of the real property associated with the scheduled appointment record may be notified. In exemplary embodiments, notification to the interested party may include providing details pertaining to the realtor associated with the realtor-client such as name, and other profile information.

Alternatively, if an offer is not accepted after a predetermined period of time has expired, the interested party or owner may be notified at step 508. This may be automated or via correspondence with an agent of the service provider. In practice of an embodiment of the invention, this step may include attempting to re-schedule another appointment date, time, and place.

Accordingly, at step 509, a determination may be made on whether a new record may be generated. For example, where a scheduled appointment record is involved, a determination may be made on whether the interested party was willing to re-schedule and thus a new scheduled appointment record was generated, or whether the interested party was unwilling or unable to commit to a new scheduled time for a meeting with a realtor. If a rescheduling was possible, method 500 may be re-initiated from step 501. Alternatively, if rescheduling was not possible, the information may be used to generate a lead—this may be useful way to recycle the information for a later time and date. If this is the case, a new or updated lead record may be generated; this lead record may be the subject of a new or updated offer record.

Figure 6:
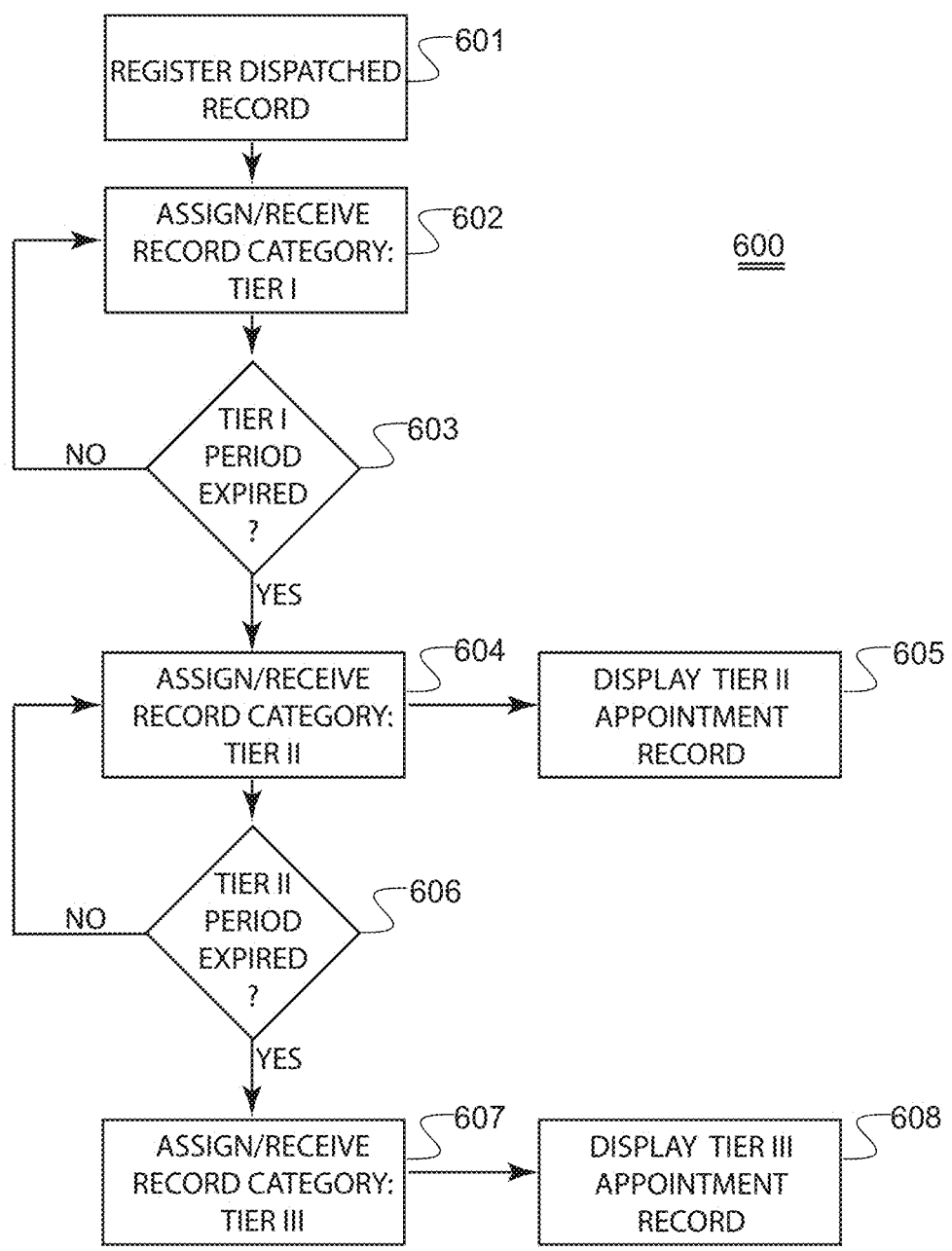
FIG. 6 illustrates a flowchart depicting a method for managing and distributing scheduled appointment records and lead records, in accordance with practice of one embodiment of the present invention.

Turning now to FIG. 6, a flowchart depicts a method for managing and distributing scheduled appointment records, in accordance with practice of one embodiment of the present invention. More specifically, method 600 involves one or more protocols of managing lead records and scheduled appointment records in order to maximize transacting opportunities. A set of protocols such as the steps described by method 600 may dictate how a lead is categorized and handled at every step—for example, how long a lead is listed, what price a lead may be offered for and to whom, and where within the system the lead will be listed. It is noted that although method 600 is shown in a particular sequence of steps, other conceivable sequence of the steps may be practiced without deviating from the scope of the present invention. Method 600 includes a set of rules, protocol or algorithm that maximizes the use of transactional opportunities such as scheduled appointments or leads. Such method may allow a service provider to re-sell records (or transactional opportunities) in the event that a first or even subsequent realtor-clients are unsuccessful. Moreover, different record categories may dictate different values or prices at which an offer record may be sold or auctioned.

In step 601 an offer record that has been dispatched or accepted by one or more realtor-clients may be registered or confirmed as dispatched. Accordingly, in exemplary embodiments, the acceptance or delivery of an offer record to a client device may trigger a set of protocols dictated by a lead tier or record category that has been assigned to each lead record, scheduled appointment records, and thus each offer record.

In step 602, a first record category (e.g. Tier I) associated with the offer record may be assigned or received. This may include, without limitation, determining or triggering a particular time period associated with said first record category.

In step 603, a determination may be made as to whether the first predetermined period has lapsed before the realtor was successful in consummating the proposed transaction associated with the lead record or scheduled appointment record subject of the offer record dispatched inn step 601. In the event that the realtor-client is unable to obtain a successful transaction from the lead record or scheduled appointment record, the termination of the first predetermined period (for example, 30 days) may trigger a re-categorization so that the lead record or scheduled appointment record may be re-categorized in step 604 below for an alternative use such as an alternative type of offer, or even a similar offer, which may be provided to a second realtor-client.

In step 604, after the first predetermined time period associated with the first record category has lapsed (for example after the 30 days), the system may categorize the record associated with the first offer record under a second category such as Tier II. This may include assigning or receiving a second predetermined period associated with the second record category or lead tier II, and may include changing the offer type. For example, an offer type 'individual' that may have been previously associated with the offer record accepted by a first realtor-client who was unsuccessful, may then be re-categorized to include an offer type 'market' and offered to a second realtor-client. In exemplary embodiments, Tier II records may be displayed as a current top lead that may be sold at an early stage to a second realtor-client at the top rate for the duration of the second predetermined period of time applicable to Tier II records (for example, 7 days). Accordingly, offer records concerning lead records or scheduled appointment records in Tier II may be displayed via the GUI to other users at step 605, even though a lead record or a scheduled appointment record was originally provided to the first realtor-client that accepted the first offer record.

In step 606, a determination may be made as to whether the second predetermined period has lapsed. In the event that the second realtor-client is unable to obtain a successful transaction from the lead or scheduled appointment, a lapse of the second predetermined period (for example, 7 days) may trigger a re-categorization so that the lead record or scheduled appointment record is categorized yet again.

In step 607, after the second predetermined period has lapsed, the system may categorize the lead record or scheduled appointment record under a third category such as Tier III. In exemplary embodiments, Tier III records may be instead displayed to a third realtor-client or even to several other realtor-clients; this may be achieved by providing the offer record to multiple realtor-clients simultaneously. For example, in one embodiment, Tier III records may be made available to up to five different relator-clients.

Accordingly, in step 608, an offer record in Tier III may be displayed via the GUI to other realtor-clients.

It should be noted that in exemplary embodiments, every time a record is purchased, the record is taken off from view of other realtor-clients. Further, every time a record is categorized (or a predetermined period has lapsed), the record may be returned to the service provider for review and re-qualification. Furthermore, only three tiers or three categories are shown as an example, but more or less categories may be implemented without deviating from the scope of the present invention.

Figure 7:
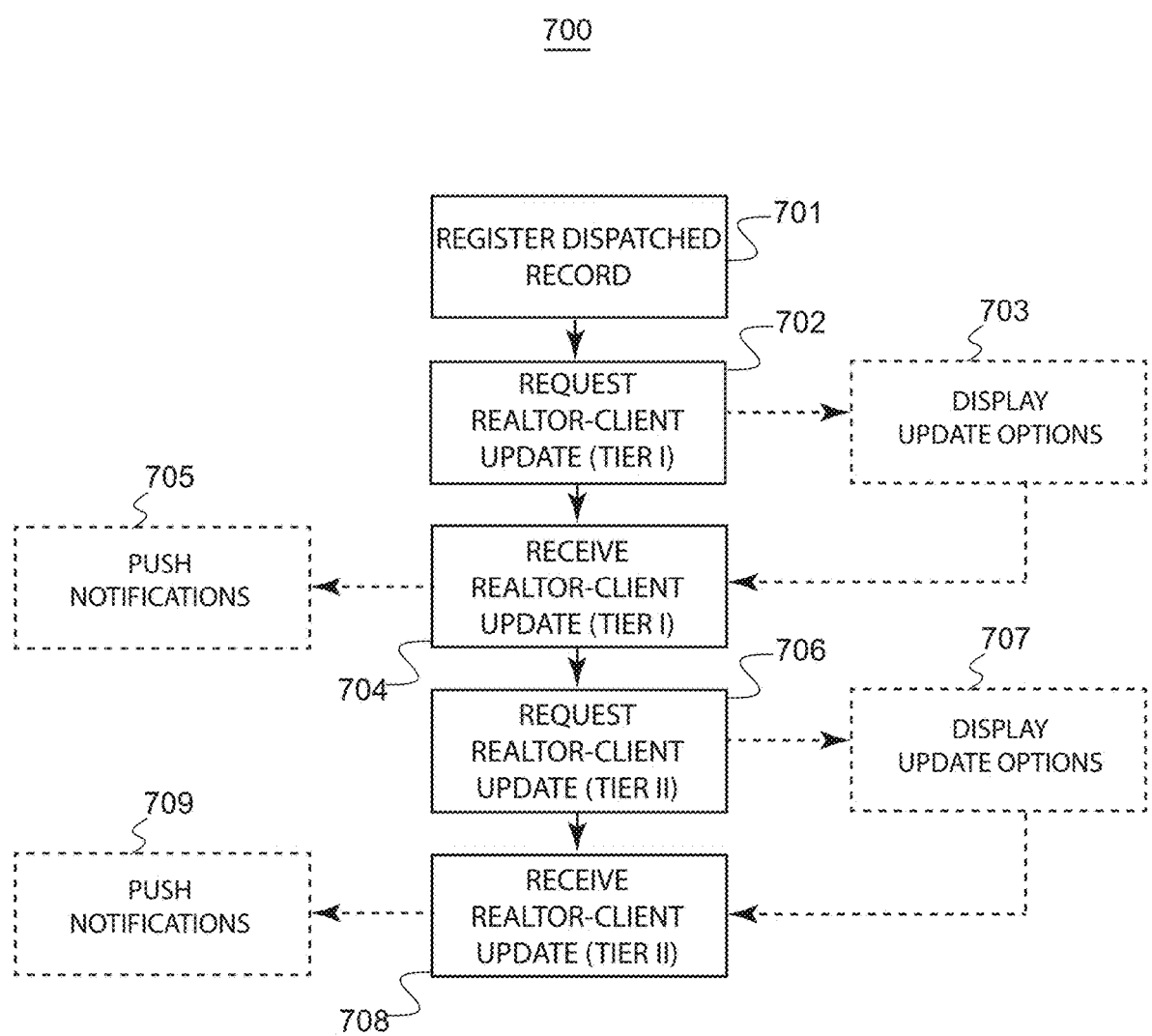
FIG. 7 illustrates a flowchart depicting a method for distributing information concerning scheduled appointment records and other transactional opportunities, in accordance with practice of one embodiment of the present invention.

Turning now to the next figure, FIG. 7 illustrates a flowchart depicting a method for gathering information concerning leads, scheduled appointments, and other transactional opportunities, in accordance with practice of one embodiment of the present invention. In an exemplary embodiment, method 700 comprises: receiving or accessing a dispatched appointment record (701); requesting a first update from a realtor-client concerning a Tier I record (702); displaying update options via a GUI (703); receiving a realtor-client update concerning the Tier I record (704); pushing notifications to the Tier I realtor-client (705); requesting a second update from a realtor-client concerning a Tier II record (706); displaying update options via a GUI (707); receiving a realtor-client update concerning the Tier II record (708); and pushing notifications to the Tier II realtor-client (709).

To explain the steps above, method 700 concerns the interactions between the system and the realtor-clients that purchase offer records associated with lead records and scheduled appointment records. Although only lead tiers I and II are discussed, this method may be implemented throughout the life of a record in order to receive valuable feedback from the realtor-clients that handle the leads and scheduled appointments.

In step 701, an offer record that has been dispatched or accepted by one or more realtor-clients may be registered or confirmed as dispatched.

In step 702, a request from the service provider to the realtor-client may be provided via the GUI. For example, this may include providing a GUI that displays update options every time a predetermined period is initiated at the outset of a lead tier (such as tier I). As will be discussed below with reference to an exemplary GUI, this may be achieved by providing banners, messages, or menus that request for user feedback from each realtor-client.

In step 703, accordingly, a GUI may display one or more options that request information or feedback from the user. For example, see FIG. 18 and FIG. 19.

In step 704, the user feedback may be received, stored, and analyzed. This information may be useful at a later time to better match the realtor-client with other potential offer records including leads and scheduled appointments for which the realtor-client may have a high probability of success. Furthermore, in step 705, useful tips and information may be offered to the realtor-client currently handling the lead.

In step 706, further updates may be requested from the same or other realtor-clients that are currently handling the same or alternative offer record concerning the same lead, which is now in its second predetermined period or lead tier II.

Similarly, in step 707, a GUI may display one or more options that request information or feedback from the realtor-client(s); and in step 708, the user feedback may be received, stored, and analyzed. Again, these continuous updates concerning the development of the same lead may be useful for optimizing the system. Furthermore, in step 709, additional useful tips and information may be offered to the realtor-client currently handling the lead.

Figure 8:
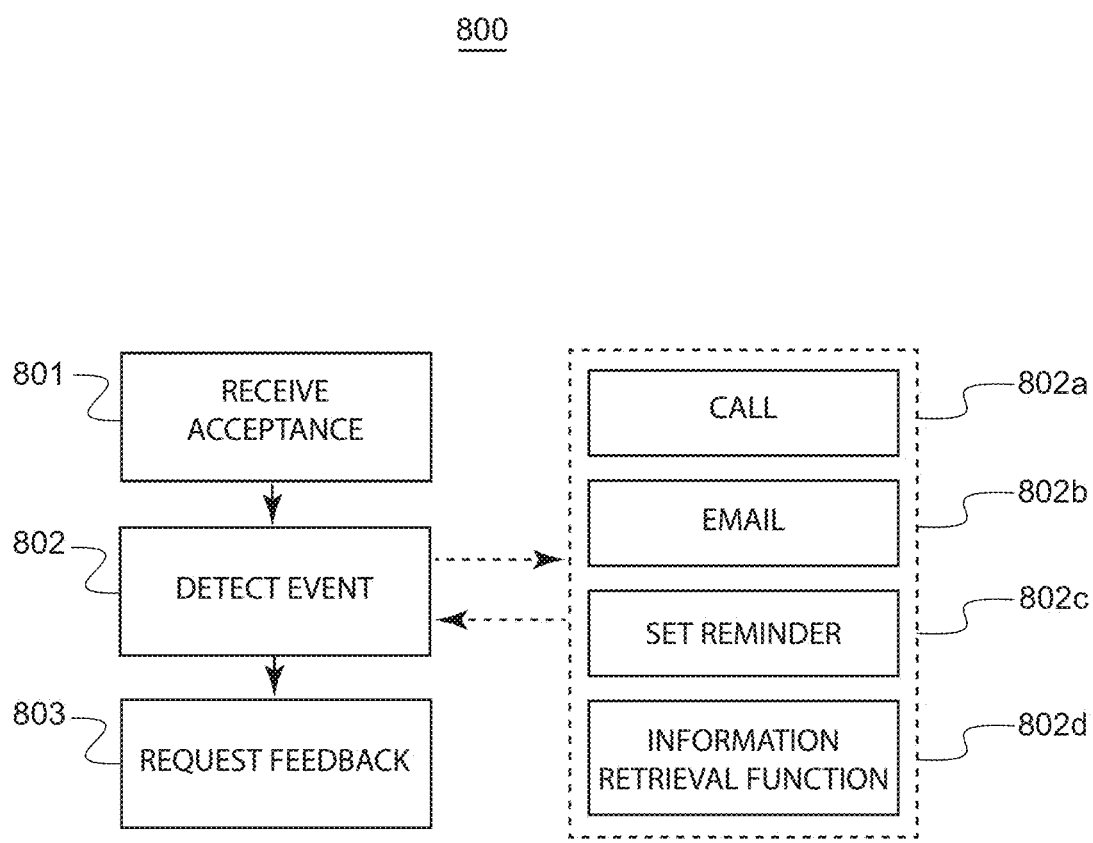
FIG. 8 illustrates a method for gathering user data associated with the transacting of scheduled appointment records and lead records, in accordance with practice of one embodiment the present invention.

FIG. 8 illustrates another method for gathering user data associated with the transacting of scheduled appointment records, in accordance with practice of one embodiment the present invention. In exemplary embodiments, the system may be configured to retrieve as much useful information from its users as possible in order to better match users with interested parties and generate new leads. This way, the system can be configured to optimize itself by continuously learning from its users about their experiences. To these ends, method 800 describes one method that may be implemented with a system in accordance with the present invention. It is noted that although method 600 is shown in a particular sequence of steps, other conceivable sequence of the steps may be practiced without deviating from the scope of the present invention.

In step 801, an acceptance of a lead record or scheduled appointment record may be confirmed or received by the system. This may include receiving confirmation that an offer has been accepted and an offer record concerning a lead or scheduled appointment record has been purchased or assigned to a particular realtor-client.

In step 802, specific events or actions taken by the user assigned to a particular scheduled appointment record may be detected. For example, and without limiting the scope of the present invention, the system may detect different calls to action such as initiating a call 802*a* sending an email correspondence 802*b*, setting a reminder for a particular task 802*c*, executing an information pulling function 802*d*, or any other action taken by the realtor-client for the purpose of furthering efforts to consummate a transaction opportunity associated with the scheduled appointment. Detecting these actions from a realtor-client may be helpful to track the realtor-client's progress, but also offer a unique opportunity to aid the realtor-client with suggestions or guidance, as well as obtain information pertaining to feedback from the realtor-client's experience.

A call 802*a* may be any call that is initiated by the realtor-client—this may include a call from the realtor-client to the interested party to introduce themselves and verbally confirm the appointment date. This may be detected by the GUI in several ways. In one embodiment, the user interface offers a means to initiate the call so that the action may be recorded. In other embodiments, the user interface may request the realtor-client to indicate whether the initial call was made.

An email correspondence 802*b* may be any email that is initiated by the realtor-client—this may include sending an initial or follow-up email correspondence from the realtor-client to the interested party. This may be detected by the GUI in several ways. In one embodiment, the user interface provides a means to initiate the email so that the action may be recorded. In other embodiments, the user interface may request the realtor-client to indicate whether the email was sent.

Setting a reminder 802*c* may be any reminder that the realtor-client sets and which is associated with a task concerning the scheduled appointment record—this may include a reminder to follow-up with another call, a reminder for a follow-up meeting, or even the initial reminder for the initial meeting subject of the scheduled appointment record. This may be detected by the GUI in several ways. In one embodiment, the user interface provides a reminder function which may be associated with each record and may be recorded. In other embodiments, the user interface may request the realtor-client to indicate whether the reminder was set.

An information retrieval function 802*d* may be any information gathering technique, such as database searches, that may be implemented by the realtor-client—this may include accessing multi-listing services and pulling or retrieving data such as comparative market analysis data. These actions may be detected by the GUI in several ways. In one embodiment, the user interface offers a means to initiate such functions and thus the action may be recorded. In other embodiments, the user interface may request the realtor-client to indicate whether the information was retrieved.

Naturally, other actions that may be expected or helpful to each realtor-client may be tracked in a similar manner.

In step 803, upon detecting or confirming that a particular action has been taken by the realtor-client, a request for feedback from the realtor-client may be made. For example, a simple rating request may be provided so that the realtor-client rates their experience. Additionally, specific questions geared towards a particular call of action may be provided to each realtor-client. Furthermore, comments from the realtor-client may be requested to obtain more specific information. One example of a user interface is provided in FIG. 19 below, which may be used to gather information from each realtor-client at step 803. This way, the system may be configured to retrieve as much useful information from its realtor-clients as possible in order to better match realtor-clients with interested parties and generate new leads.

Figure 9:
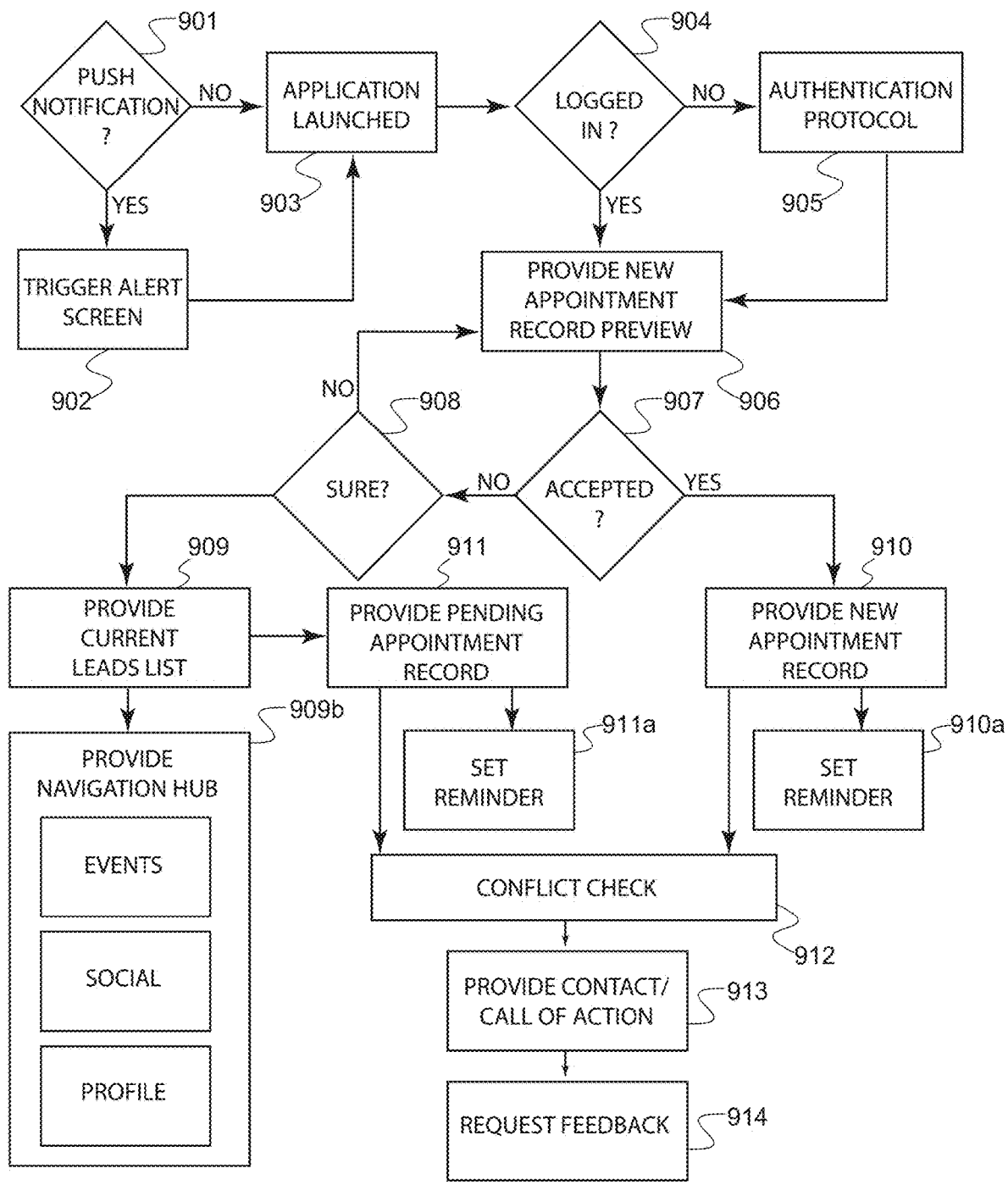
FIG. 9 illustrates a method for distributing scheduled appointment records or lead records via a user interface on a client device, in accordance with practice of one embodiment of the present invention.

Turning now to FIG. 9, a method for distributing scheduled appointment records or leads via a user interface on a client device, in accordance with practice of one embodiment of the present invention, is discussed. More specifically, method 900 depicts one embodiment of how a scheduled appointment record may be offered to a realtor-client via a client device that includes a mobile application in accordance with the present invention. As noted with other methods, the steps and particular sequence of steps in method 900 is only illustrative, and other sequences may be possible without deviating from the scope of the present invention.

In step 901, the system may notify the realtor-client of an existing offer associated with a scheduled appointment record. Because the realtor-client has previously installed a mobile application provided by the service provider, the realtor-client may or may not have enabled push notifications. Accordingly, a client device with enabled push notifications may receive a notification alerting the realtor-client of the offer at step 902. If this is the case, notifications or alert screens associated with the offer may be configured to automatically launch the mobile application at step 903 using well known techniques.

Alternatively, a realtor-client may be required to manually launch the mobile application (903), which may be configured to provide an alert, a badge, a banner, or any other known indicator that notifies the realtor-client of the pending offer.

At step 904, a determination confirms a login status of the realtor-client. If the realtor-client is already signed in, the offer may be provided via the GUI at step 906. If the realtor-client is not logged in, or is their first time logging in to the mobile application, then one or more authentication protocols may be initiated at step 905. For example, this may typically require username, password creation, and profile information input. In some embodiments, the service provider may use this step to associate the realtor-client to their membership class or membership type (or assign a role ID), which may have already been established prior to signing up on the mobile application. Accordingly, each realtor-client may be provided with a set of privileges or access permissions that depend on the membership class or status of the realtor-client and which are associated with a role ID.

In step 906, the offer record may be provided including a predetermined time period to accept the offer record. In some embodiments, determinations at steps 907 and 908 may provide a time frame during which to accept the offer record, decline the offer record, or time frame to reconsider whether to decline (e.g. see FIG. 21). If the offer record is accepted, the scheduled appointment record may be fully disclosed in step 910. If the offer is declined, then at step 909 the realtor-client may be guided to a main hub of the mobile application, such as a view of their current lead list.

In step 909, where the realtor-client declines the offer record, a list of current and or past leads and scheduled appointment records may be provided via the GUI. Furthermore, declining an offer record may take the realtor-client to a main hub or navigational options typically available via the GUI so that the realtor-client may easily engage with currently active leads and or other features, services offered via the GUI (e.g. see FIG. 15).

Alternatively, in step 910 the lead record or scheduled appointment record—or all information associated with each record—may be fully disclosed (e.g. see FIG. 16), providing all information required by the realtor-client to initiate contact with the interested party, confirm the scheduled appointment on the scheduled appointment record (if a scheduled appointment record was purchased or accepted), and generally begin taking the necessary actions to successfully close on the transactional opportunity.

As will be explained further below with reference to specific examples of the user interface, once a realtor-client is viewing a current record—such as a newly accepted scheduled appointment record (910), or a previously accepted appointment record (911)—several options will become available to the realtor-client. One such function may include setting reminders associated with each record (for example at steps 910a or 911a). As explained above, this may include setting a reminder for a particular task such as an initial call or simply a reminder for a pending scheduled appointment or follow-up meeting.

Other useful functions may include running a conflict check to remind or alert the realtor-client of potentially conflicting meetings or events for which the realtor-client has already set aside times. Accordingly, at step 912, a conflict check may be triggered and the GUI may display a warning banner, notification indicator, or other indicating objects via the GUI to alert the realtor-client to check of a potential conflict (e.g. see FIG. 16, FIG. 18).

By step 913, a realtor-client typically has access to several calls of action or functions that enable the realtor-client to move towards successfully closing the transactional opportunity. For example, step 913 may include facilitating a call, email, or other correspondence, or facilitating information retrieval.

Figure 19:
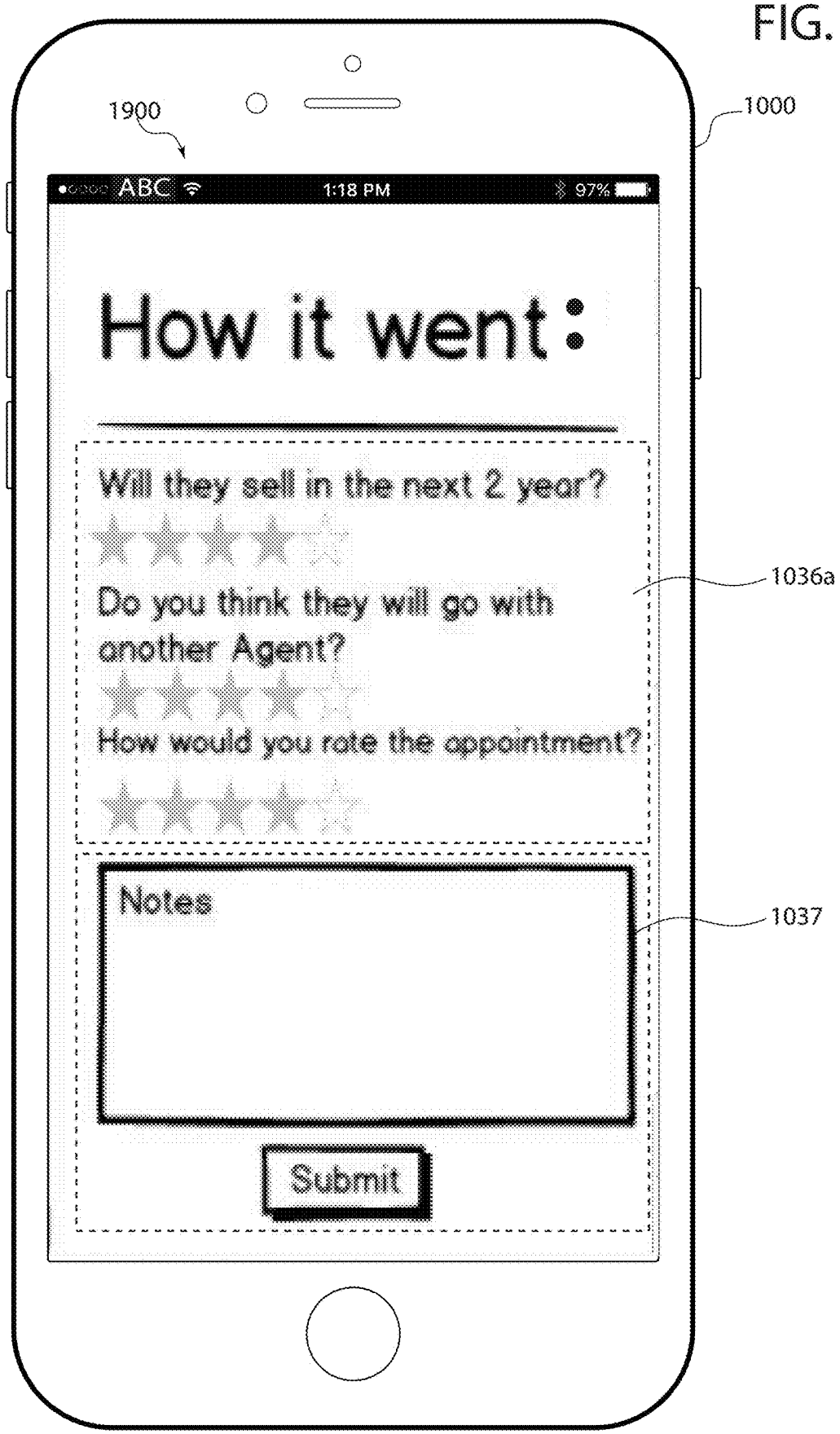
FIG. 19 illustrates an exemplary interface for requesting user data associated with one or more transactions of scheduled appointment records.

In step 914, any action that was taken by the realtor-client may be followed-up with a request for feedback (e.g. see FIG. 19).

The remaining figures disclose an exemplary GUI for facilitating the transacting of scheduled appointments or leads. The figures show several embodiments. For example, FIG. 10-FIG. 24 illustrate several embodiments of a GUI, which may be provided via a mobile device application; these figures are discussed in turn.

Figure 10:
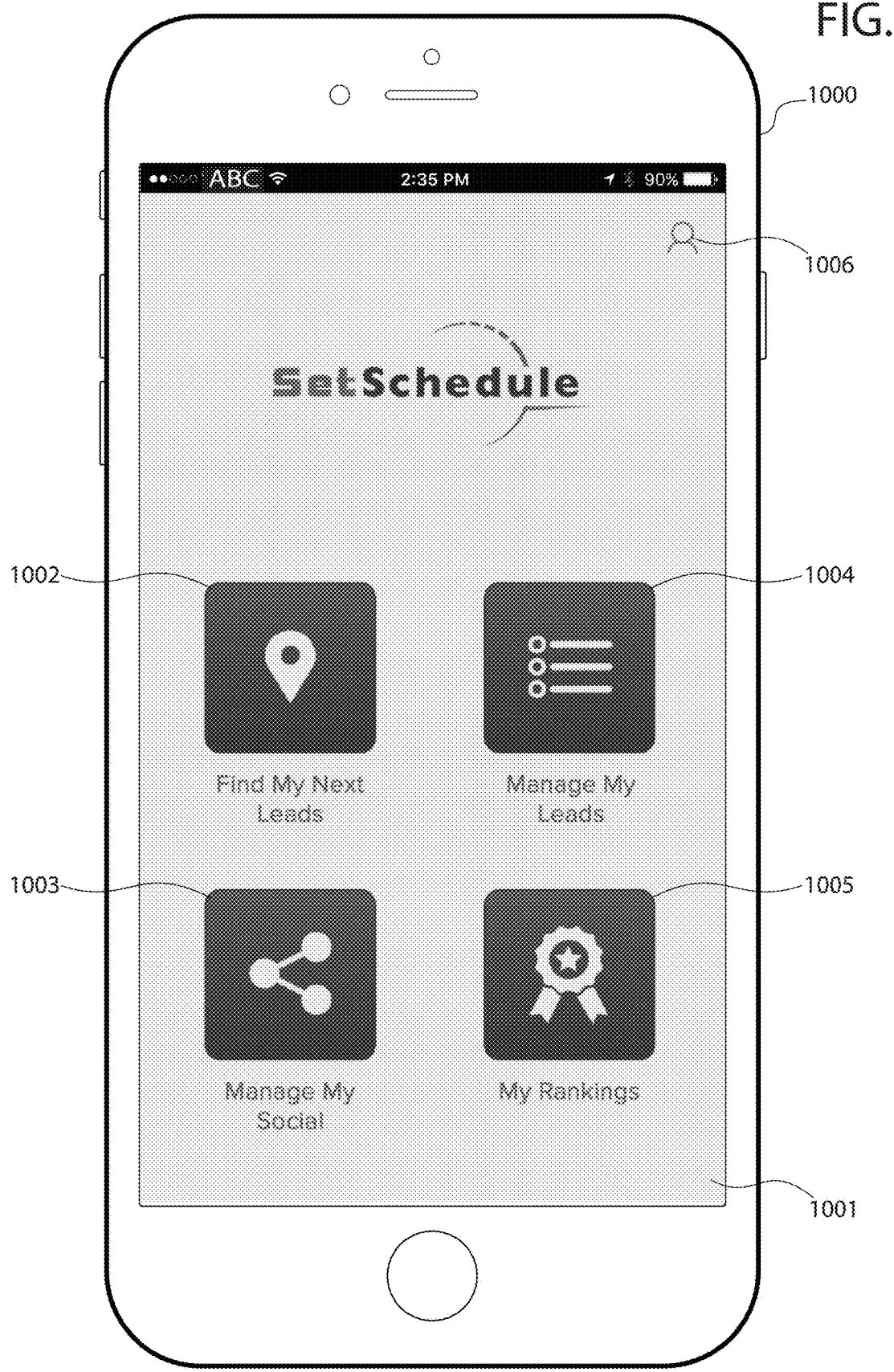
FIG. 10 illustrates an exemplary dashboard for a GUI configured for transacting scheduled appointment records, in accordance with one embodiment of the present invention.

FIG. 10 illustrates an exemplary dashboard for a GUI configured for transacting lead records or scheduled appointment records, in accordance with one embodiment of the present invention. The idea for the dashboard is to create a landing "friendly" and simple "call for action" page with windows and buttons. The main windows may serve as a landing page or main control page that offers a gateway to menus or sub-menus. More specifically, FIG. 10 illustrates client device 1000 which may be a mobile device or smartphone. Naturally, client device 1000 may be a desktop computer, a tablet, a smartphone, or any other device suitable for running a GUI such as a desktop application, a mobile application, a browser suitable for accessing a website, or any other suitable software for accessing a GUI in accordance with the present invention.

Typically, client device 1000 runs a GUI that includes a touch-screen interface 1001, which may display a start-screen, landing page or dashboard. In such exemplary embodiment, the GUI may provide various data objects such as tabs, buttons, or navigation tools 1002, 1003, 1004, 1005, and 1006.

Button 1002 is titled (as shown) "Find My Next Leads" and may enable various functions and tools for a realtor-client to identify potential lead records or scheduled appointment records. Button 1003 is titles (as shown) "Manage My Social" and may enable various functions and tools for a realtor-client to manage posts, newsfeeds, and other social media tools available via the GUI. Button 1004 is titles (as shown) "Manage My Leads" and may enable various functions and tools for a realtor-client to manage currently and previously active leads that have been purchased or accepted, or are otherwise available via the GUI. Button 1005 is titles (as shown) "My Rankings" and may enable various functions and tools for a realtor-client to manage their progress with respect to their active leads. Button 1006 may provide access to a profile page for a realtor-client to manage and update their profile available via the GUI.

Figure 11:
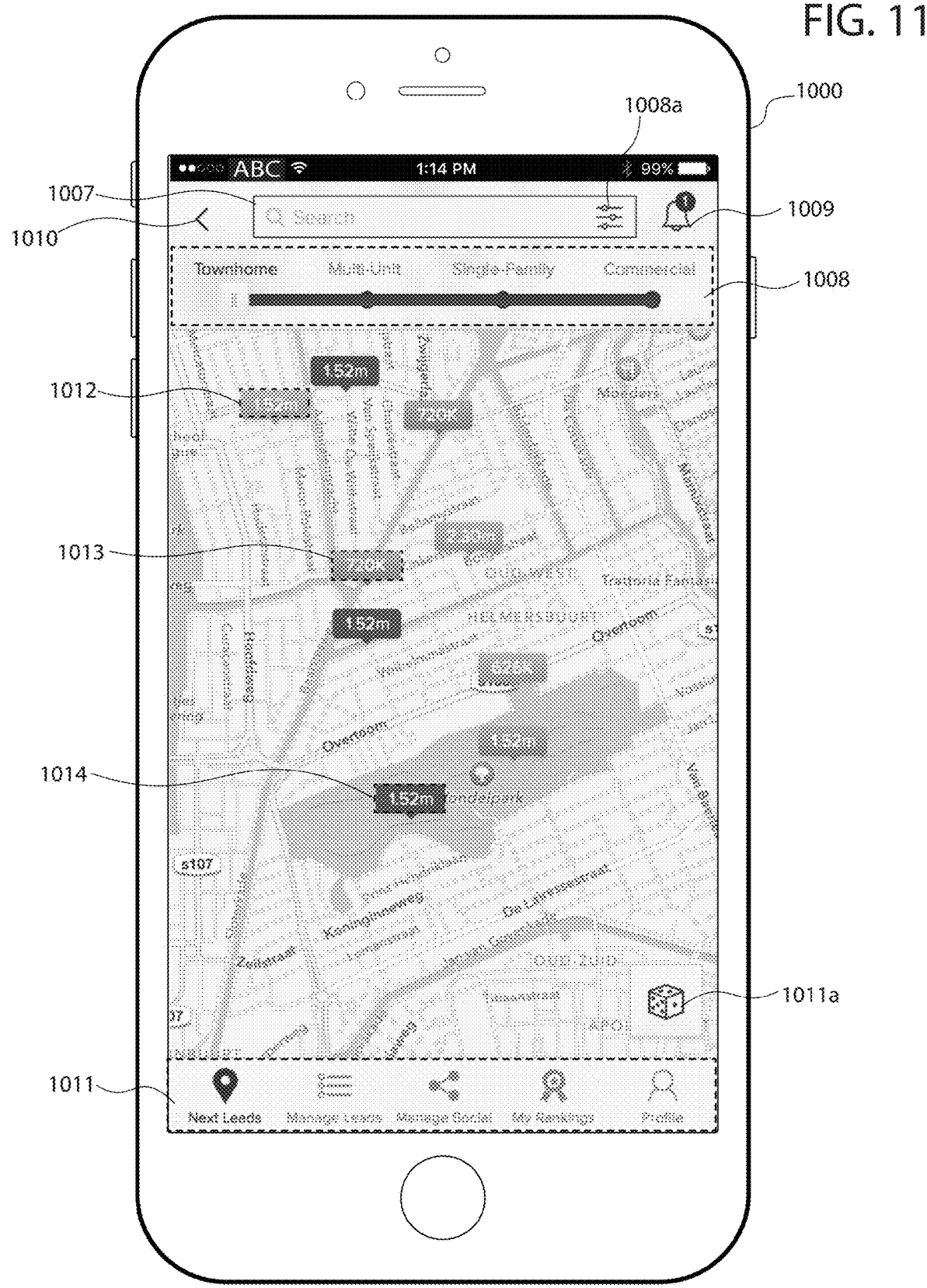
FIG. 11 illustrates an exemplary location-based interface for providing client devices with available scheduled appointment records, lead records, or other transaction opportunities, in accordance with one embodiment of the present invention.

FIG. 11 illustrates an exemplary location-based user interface for providing client devices with available scheduled appointment records or transaction opportunities, in accordance with one embodiment of the present invention. A realtor-client may navigate to this screen via the button 1002 which may enable find, search, sort and filter options to aid a realtor-client in selecting their next lead or scheduled appointment record.

In the illustrated embodiment, the GUI provides search function 1007 for searching a particular geographic region, and may include filter function 1008a (e.g. see also FIG. 12) or an onscreen filter function 1008 to aid the realtor-client's search. Other features that may be implementing using known techniques include reminder function 1009, navigational functions 1010 and 1011, and a "do you feel lucky" function 1011a.

Navigational function 1011 may include a menu or (as shown) a navigational pane that provides a type of site map for the GUI. From this navigation tool a realtor-client may typically access all the most often used features provided by the GUI such as those presented at the landing page or dashboard. Of course, other means of navigation may be implemented without deviating from the scope of the present invention.

In an exemplary embodiment (as shown) a map layout may be provided, which shows several transactional opportunities that may comprise qualified leads or scheduled appointment records offered to the realtor-client.

In exemplary embodiments, only the types of records available to a realtor-client under a previously existing membership agreement will be displayed. This may be useful to ensure that each realtor-client only receives targeted qualified leads or scheduled appointment records that they are qualified to accept.

In exemplary embodiments, different color coded indicators may be provided to indicate important characteristics of each record. For example, and without limiting the scope of the present invention, Tier I records comprising scheduled appointment records provided exclusively to the realtor-client may be color coded red, Tier II records comprising qualified leads offered to a select or limited set of realtor-clients may be color coded yellow, and Tier III records comprising qualified lead records offered to all users may be color coded green. Of course, other means of providing this information may be practiced without deviating from the scope of the present invention, including using shapes, numbers, or any other types of identifiers to indicate the lead tiers or category of a particular offer record.

In the present embodiment, record 1012 may represent a Tier II record, record 1013 may represent a Tier II record, and record 1014 may represent a Tier I record. Selecting one of the available properties/scheduled appointments or transaction opportunities presented via this screen may lead to the screen illustrated by FIG. 13. Alternatively, selecting filter function 1008a may lead to the screen illustrated by FIG. 12 and discussed in turn.

Figure 12:
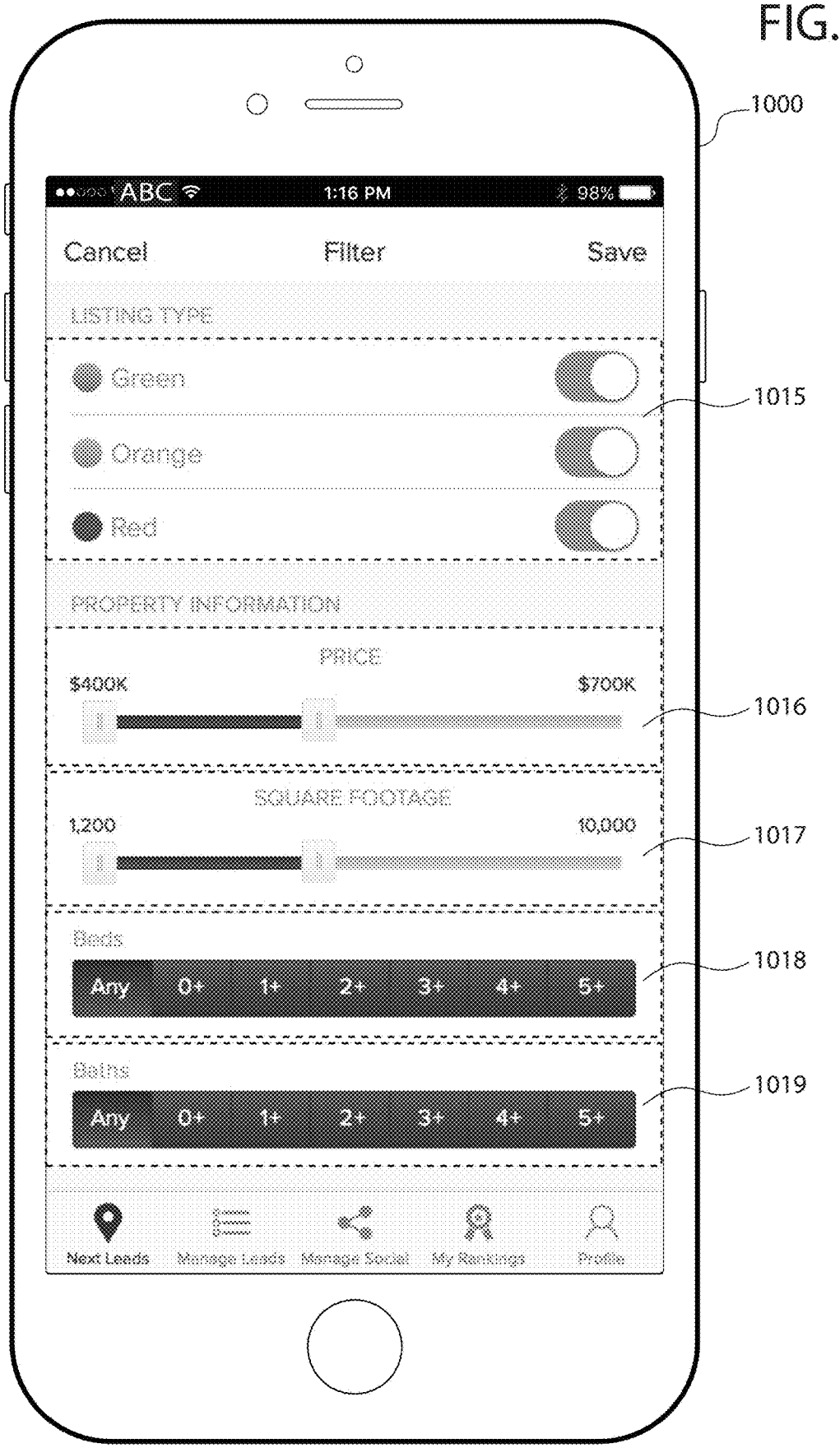
FIG. 12 illustrates an exemplary management tool interface for assisting realtor-clients with transacting scheduled appointment records, in accordance with one embodiment of the present invention.

FIG. 12 illustrates an exemplary management tool for assisting realtor-clients with transacting scheduled appointment records, in accordance with one embodiment of the present invention. For example, filters may be implemented to allow a realtor-client to select what type of transaction opportunities are displayed for that realtor-client. As mentioned above, scheduled appointment records may be categorized in different ways to maximize and monitor each transactional opportunity. Via an exemplary interface such as the one illustrated, realtor-clients may be allowed to glean or even search exclusively for a particular category of transactional opportunities.

Tools that may be made available to realtor-clients via this interface or filter function 1008a may include, without limitation: enabling or disabling a view of one or more Tiers of records (tool 1015); selecting a price range tool 1016; selecting a square footage tool 1017; a bedroom selection tool 1018; a bathroom selection tool 1019; and any other selection tools that help a realtor-client narrow or broaden a search for a particular type of lead or property.

FIG. 13 illustrates an exemplary user interface, in which some of the details of a particular transactional opportunity may be displayed. The displayed information may include photographs, pricing information, contact information, property information, and an interface for purchasing or auctioning the transactional opportunity. Typically, the shown screen comprises the preview information associated with a lead record or scheduled appointment record and which is provided as an offer record for a realtor-client to purchase or accept, bin on, or decline. More specifically, offer record 1300 is shown.

Offer record 1300 may include image 1020, pricing information 1021, additional information 1022, property information 1023 and 1024, accept button 1025, decline button 1026, bid button 1027, and contact button 1028. While different embodiments may include more or less information than shown in offer 1300, typically specific information such as the name of the interested party or address of the property may be excluded or blurred out until after purchase or acceptance of the record. Similarly, contact button 1028 may be disabled prior to purchase. This may be desirable so that the realtor-client must accept the offer record prior to being able to contact the interested party.

As mentioned above, some offer records (particularly those involving scheduled appointment records rather than qualified lead records) may be time-sensitive and thus include a predetermined allotted time for the realtor-client to accept or decline. Accordingly, offer 1300 may further include a timer or similar feature that informs the realtor-client of the remaining time under which to accept the offer before being offered to another set of one or more realtor-clients. An exemplary embodiment of such offer record is illustrated in the next figure.

FIG. 14 illustrates an exemplary interface for providing a time-sensitive offer record associated with a scheduled appointment record. More specifically, offer record 1400 is shown, including timer 1029. In exemplary embodiments, the system may use the time of acceptance of the offer record and a time limitation associated with scheduled appointment record in order to generate an active time limit on the offer. In exemplary embodiments, this may include providing an offer record that includes a timer, or a notification may be sent to a realtor-client via client device, which includes a timer. By way of a non-limiting example, notice 1029, which includes a timer may be provided with offer record 1400.

Figure 15:
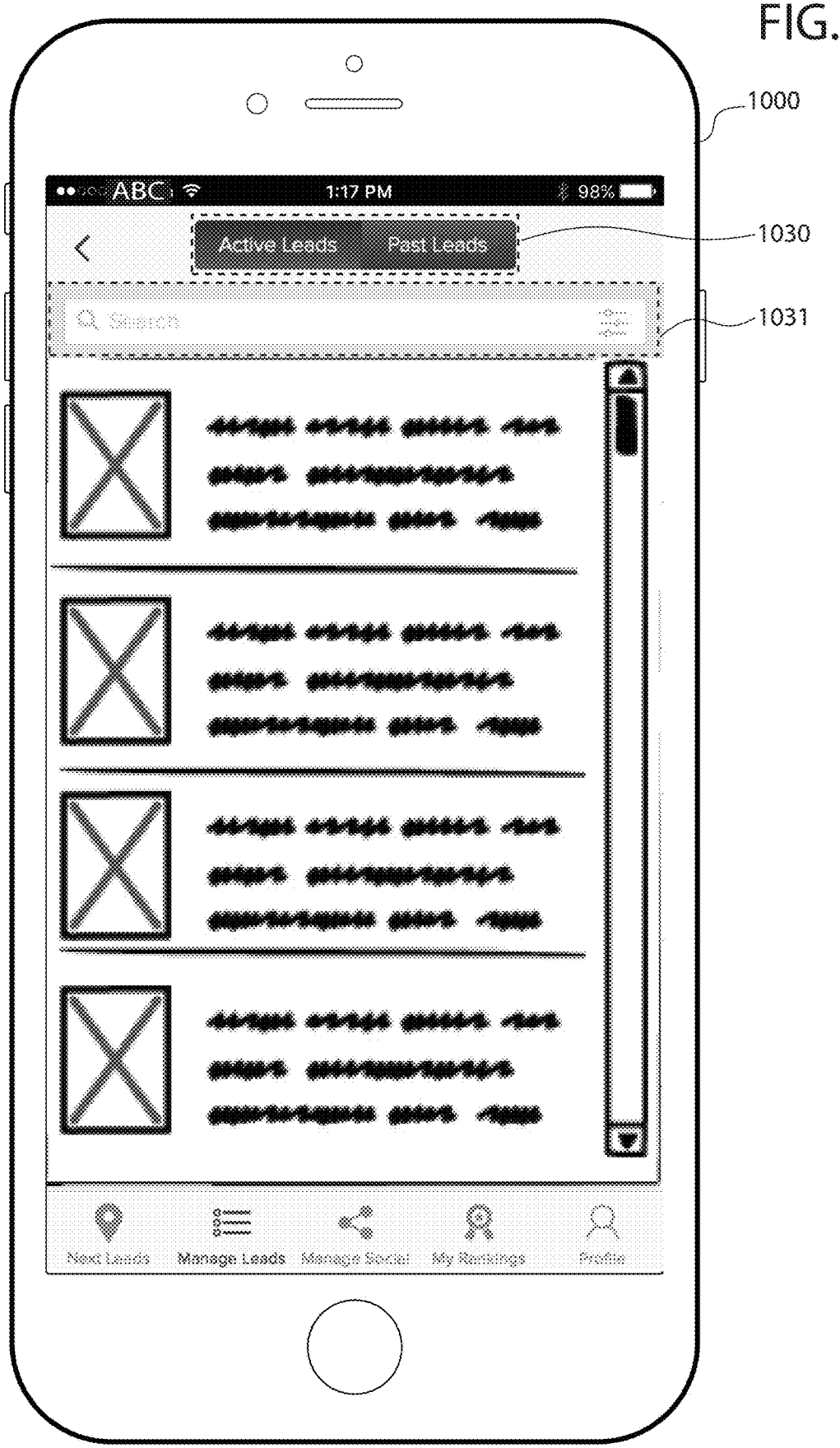
FIG. 15 illustrates an exemplary management tool for assisting realtor-clients with managing their purchased leads or purchased scheduled appointment records, in accordance with one embodiment of the present invention.

FIG. 15 illustrates an exemplary management tool for assisting realtor-clients with managing their purchased leads or purchased scheduled appointment records, in accordance with one embodiment of the present invention. Moreover, selecting "MANAGE MY LEADS" from the dashboard may guide the realtor-client to this screen. The idea is for the realtor-clients to be able to view all the lists of prior accepted leads and even upload their own. As such, the main landing page may be the list as shown FIG. 15 with a flow to the CRM client page that includes all reminders, calendars, email, text and management functions. In the embodiment shown, several tools may be provided including toggle tool 1030 for switching between viewing active and past leads, as well as a search tool 1031 for searching through a realtor-client's leads.

Figure 16:
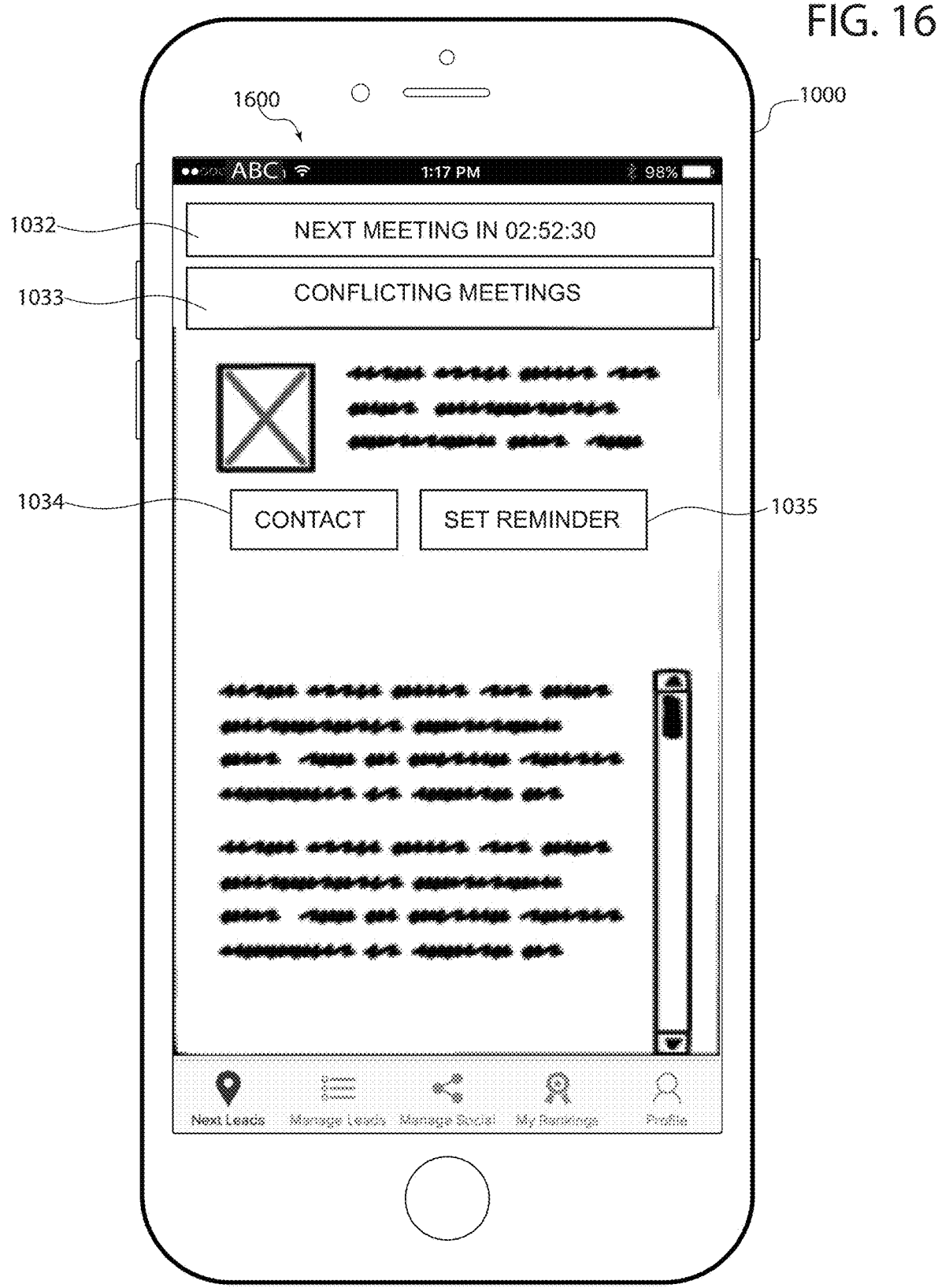
FIG. 16 illustrates an exemplary interface for facilitating the management of purchased scheduled appointment records, in accordance with one embodiment of the present invention.

FIG. 16 illustrates an exemplary interface for facilitating the management of purchased scheduled appointment records, in accordance with one embodiment of the present invention. More specifically, FIG. 16 illustrates a scheduled appointment record or record 1600. Typically, record 1600 includes all the information provided in offer 1300 and any information withheld in the offer, such as specific property information including address of the property, as well as the name and contact information of the interested party. Other features may be enabled or present for the first time, such as a means to contact the interested party as well as other useful tools including a reminder setting tool. As such, record 1600 may include contact button 1034 and set reminder button 1035 to enable said functionalities.

Additionally, other functionalities or tools may include indicators 1032 and 1033. These may be objects such as banners, labels, or buttons, that alert and inform the realtor-client of important relevant information such as an upcoming time associated with record 1600, or a time associated with another record conflicting with record 1600. Using well known techniques, indicators 1032 and 1033 may enable other functions or views that further aid the realtor-client in managing their other records.

In one embodiment, indicator 1032 may display a remaining time until the next meeting the realtor-client has previously scheduled. As such, clicking on indicator 1032 may retrieve information pertaining to that record. In another embodiment, indicator 1032 may simply display a remaining time until the next meeting associated with record 1600.

In one embodiment, indicator 1033 may display a message concerning potentially conflicting meeting. As such, clicking on indicator 1033 may retrieve a list pertaining to records that include potentially conflicting meeting times. In another embodiment, indicator 1032 may simply display a conflict associated with record 1600, only if there is indeed a potential conflict with record 1600.

As may be apparent, other embodiments and variations may be possible without deviating from the scope of the present invention.

Figure 17:
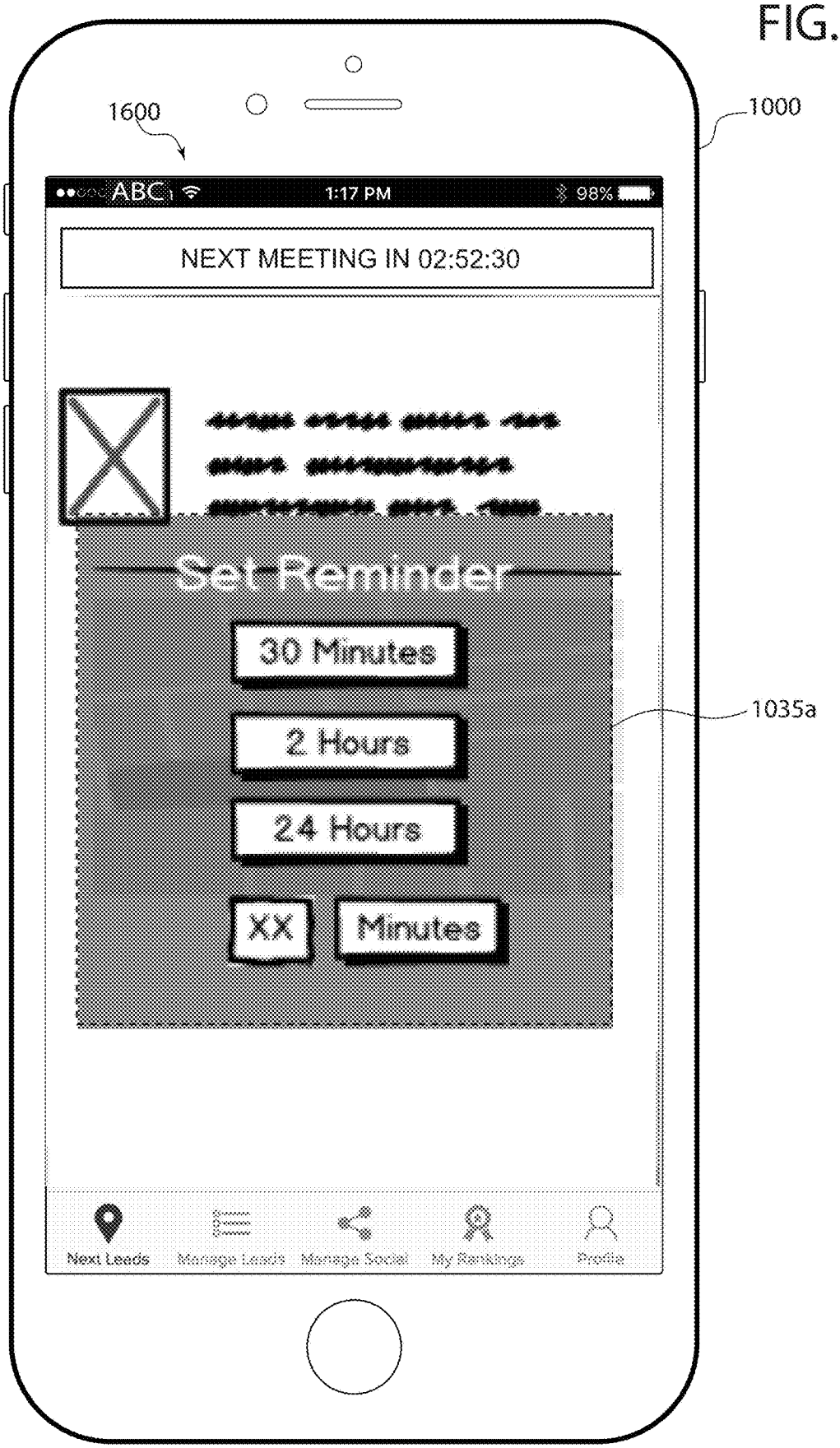
FIG. 17 illustrates another exemplary interface for facilitating the management of purchased scheduled appointment records, in accordance with one embodiment of the present invention.

Activating link or set reminder button 1035 may enable a set reminder function as explained above. FIG. 17 exemplarily illustrates such feature, in one possible embodiment of a GUI that provides for such feature. As shown, reminder function 1035a facilitates commonly used reminders within the GUI. As mentioned above, enabling functions via the GUI may aid the service provider in tracking realtor-client actions. This in turn aids the realtor-client by allowing the service provider to follow-up with suggestions, guidance, and other assistance that may benefit the realtor-client.

Figure 18:
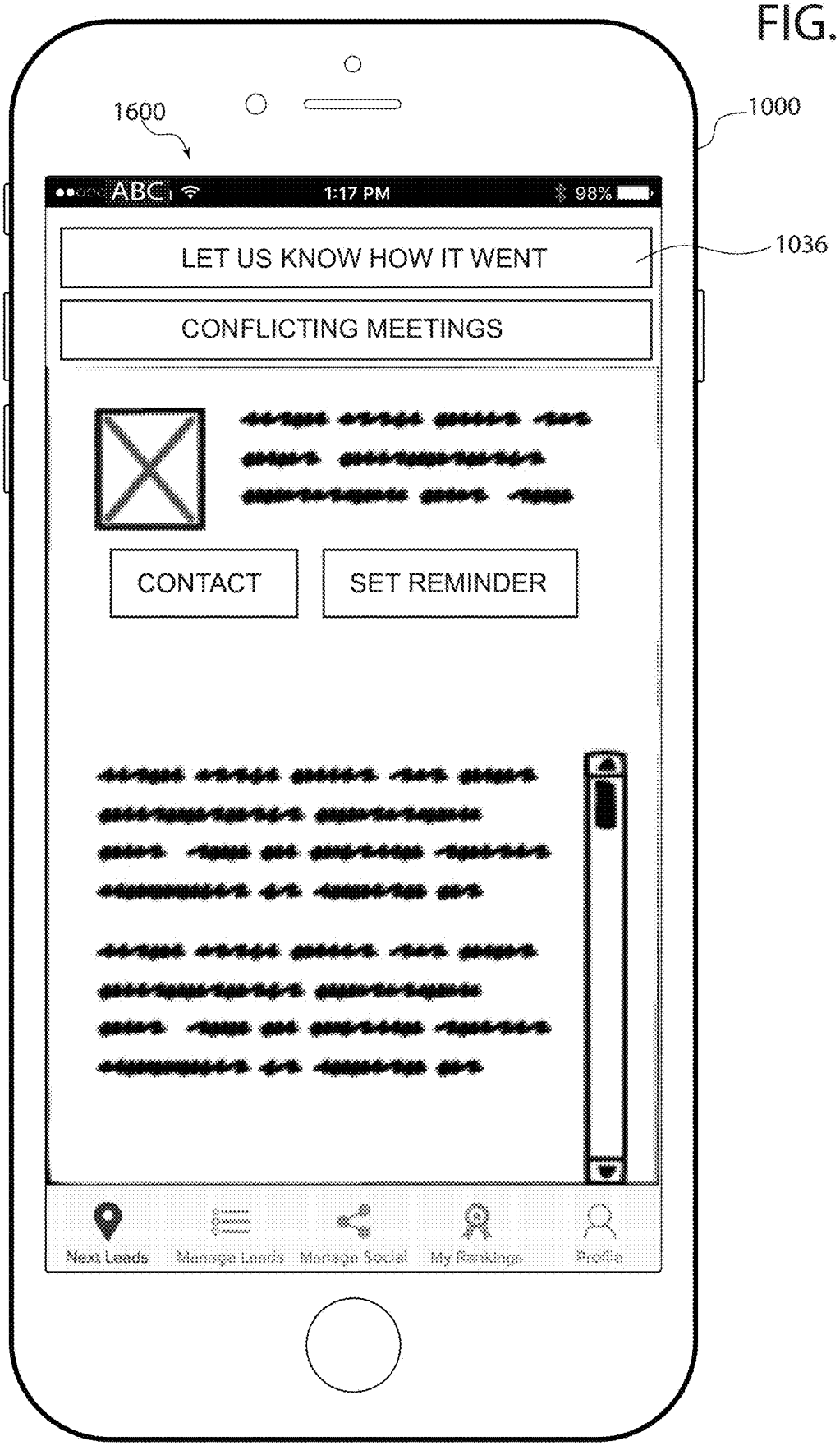
FIG. 18 illustrates another exemplary interface for facilitating the management of purchased scheduled appointment records, in accordance with one embodiment of the present invention.

To these ends, record 1600 may further include indicator 1036, which may comprise objects such as banners, labels, or buttons that alert and request feedback from the realtor-client. Accordingly, FIG. 18 illustrates another exemplary interface for facilitating the management of purchased scheduled appointment records, in accordance with one embodiment of the present invention. More specifically, FIG. 18 shows record 1600 which includes indicator 1036. Indicator 1036 may be provided after detecting that one or more actions by the realtor-client have taken place—for example as explained with reference to method 800.

In the shown embodiment, indicator 1036 includes a message that states "LET US KNOW HOW IT WENT" with a clickable object that may retrieve a list of questions, a comment box, or link the realtor-client to a different screen (e.g. see FIG. 19) where the service provider may request information about a particular event, action, or step that the realtor-client has taken towards closing the transactional opportunity. As may be apparent, other embodiments and variations may be possible and different means of obtaining feedback from a realtor-client may be implemented without deviating from the scope of the present invention.

FIG. 19 illustrates an exemplary interface for requesting realtor-client data associated with one or more transactions of scheduled appointment records. More specifically, FIG. 19 depicts feedback form 1900, which many include requests for various types of information associated with a realtor-client's experience during a particular call for action. These requests may include a request to rate performance, a request to rate the realtor-client's experience, a request for comments or notes, a request with specific questions for specific information, or any other request for information that the service provider may be interested in. In the shown embodiment, feedback form 1900 includes rate box 1036a (with a plurality of questions and statements that the realtor-client is requested to rate from a scale of one through five), and comment box 1037 for the realtor-client to input notes or comments via text.

Examples of how this feedback may be utilized by the service provider includes facilitating more successfully matches between that realtor-client with future qualified leads and scheduled appointments; facilitating more compatible matches between that realtor-client with future interested parties; providing the realtor-client with feedback to improve future interactions and success in future transactional opportunities; and overall optimize the system to better assist realtor-clients and maximize revenue stream.

Figure 20:
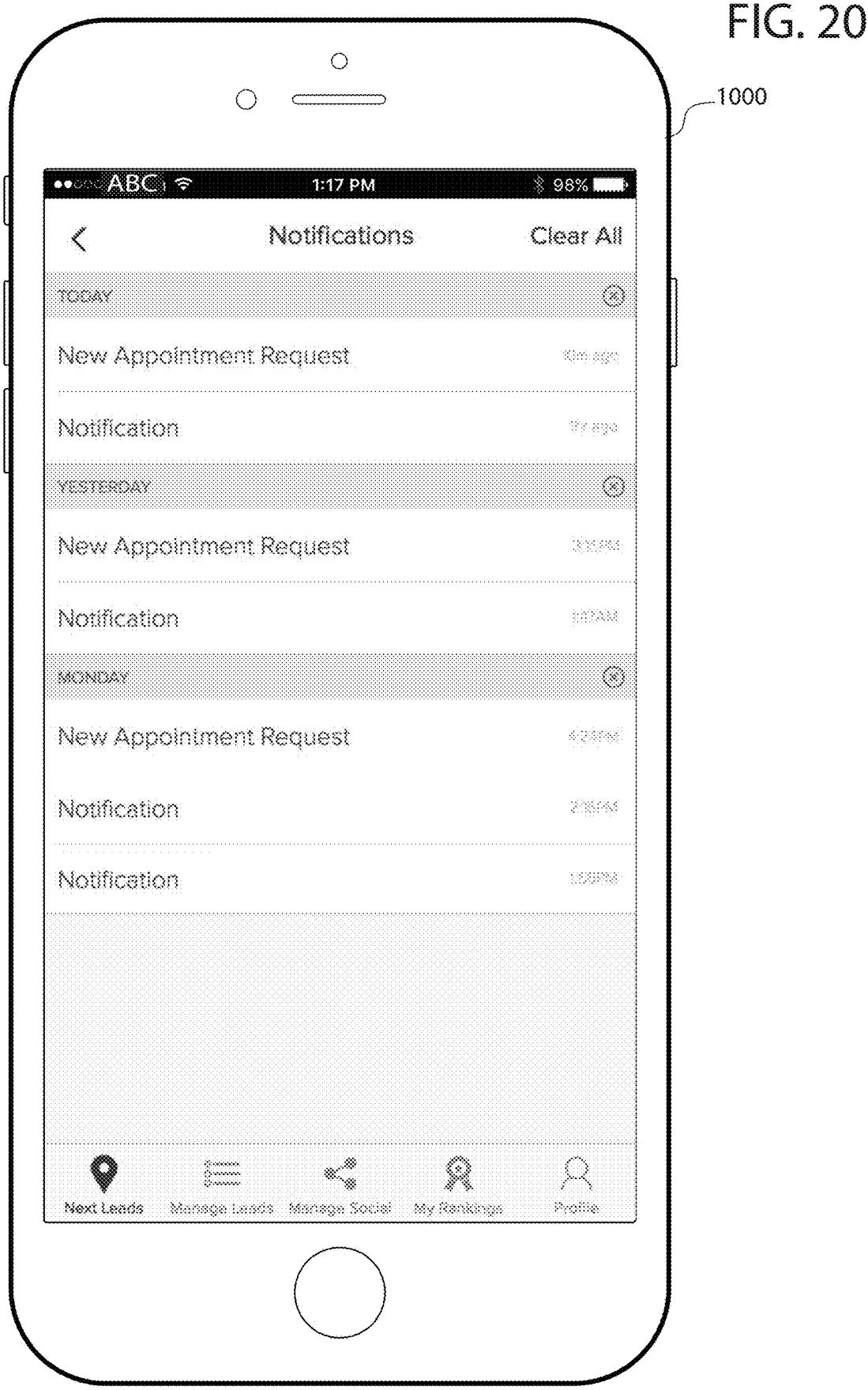
FIG. 20 illustrates an exemplary user interface configured to provide notifications concerning available transaction opportunities, in accordance with one embodiment of the present invention.

FIG. 20 illustrates an exemplary user interface configured to provide notifications concerning available transaction opportunities, in accordance with one embodiment of the present invention. For example, notification such as those discussed with reference to method 600 may be provided in this screen.

Figure 21:
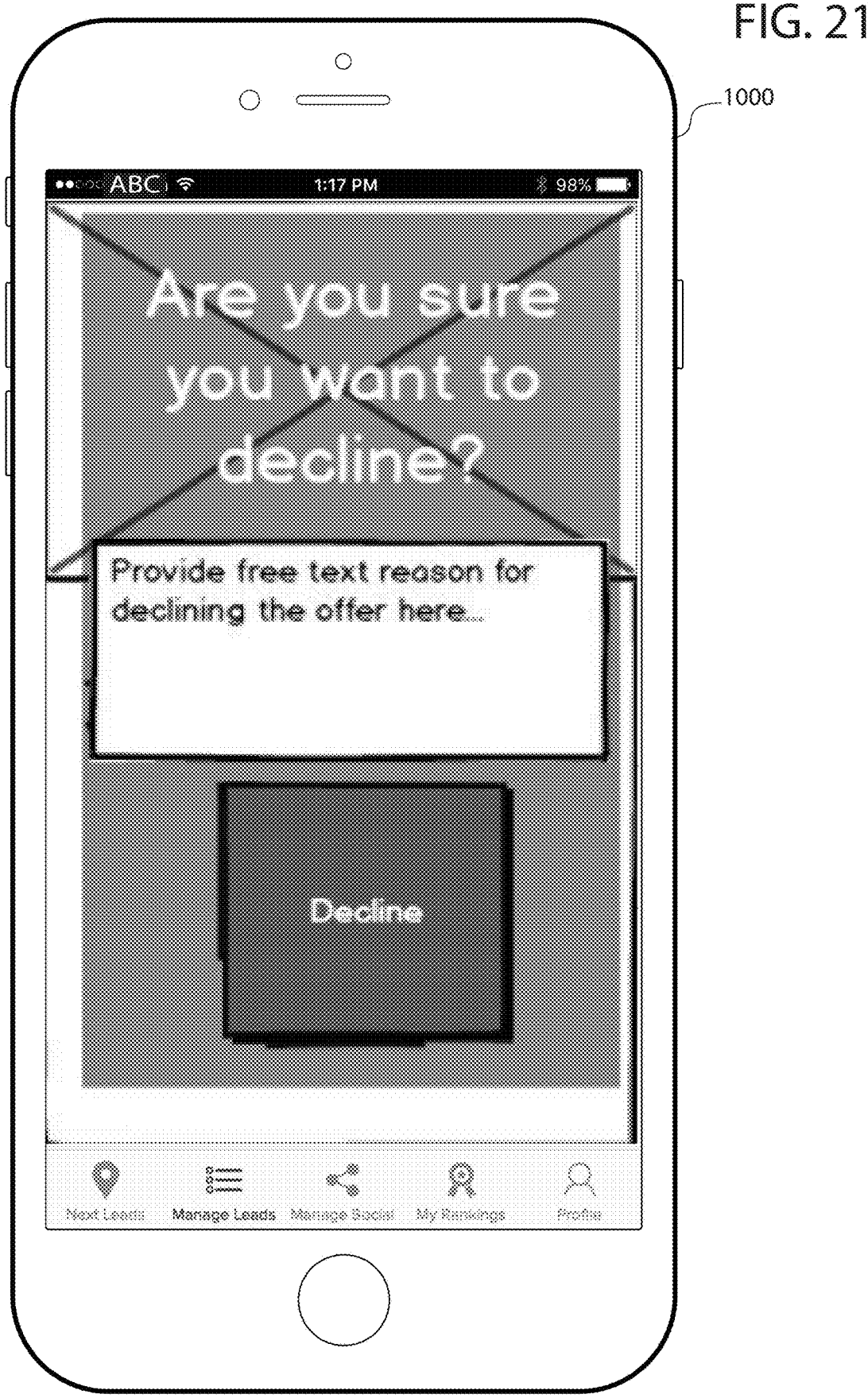
FIG. 21 illustrates an exemplary interface for requesting user data associated with one or more transactions of scheduled appointment records.

FIG. 21 illustrates another exemplary screen that may be provided to a user for feedback upon declining an offer. This information may aid the service provider by providing information that allows the service provider to learn about the particular realtor-client preferences so that future offers are better matched. Similarly, the service provider may obtain information pertaining to the property, the pricing of the offer, or any other details that may guide the service provider in optimization of the system.

Figure 22:
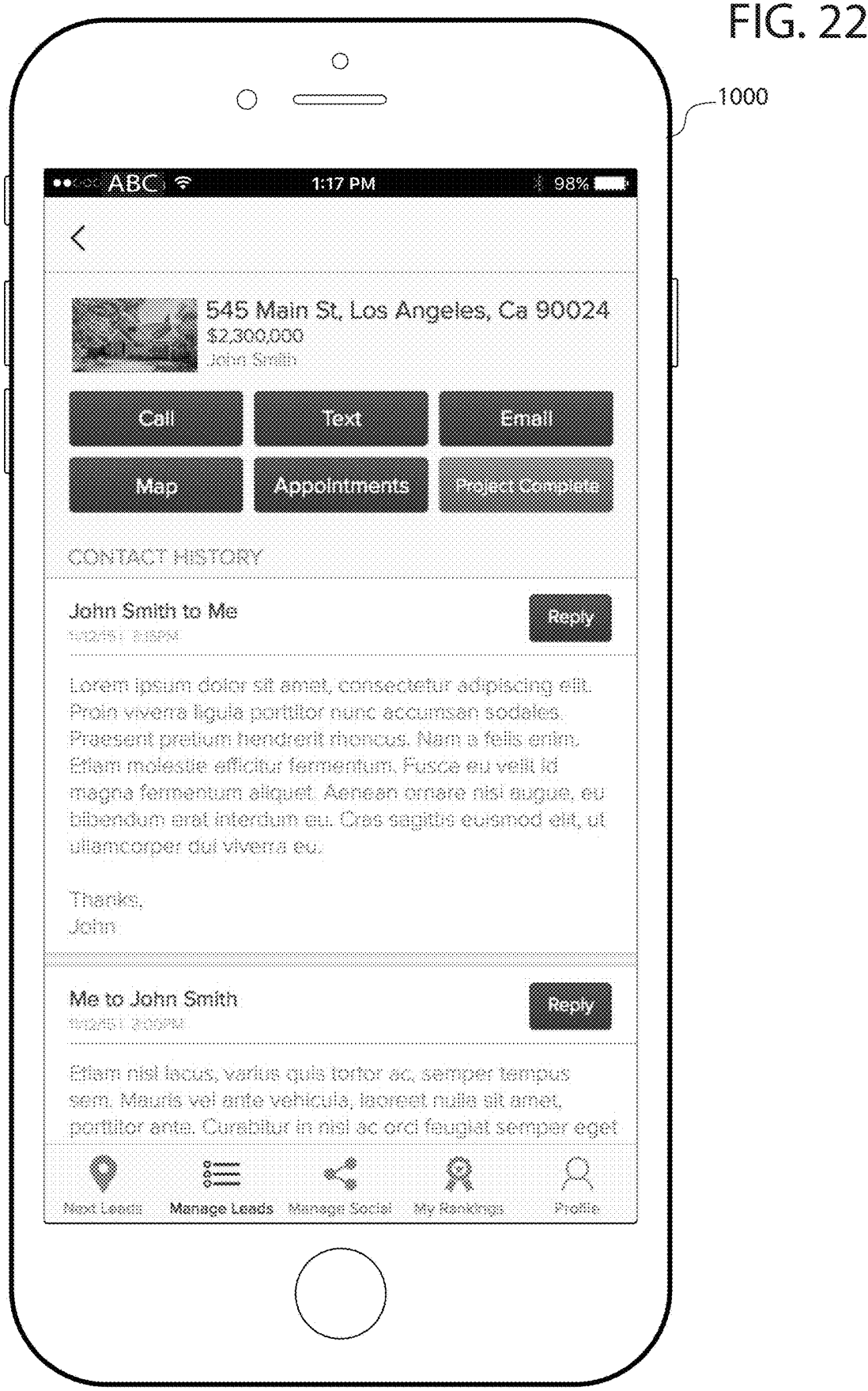
FIG. 22 illustrates another exemplary management tool for assisting realtor-clients with managing their purchased leads or purchased scheduled appointment records, in accordance with one embodiment of the present invention.

FIG. 22 illustrates another exemplary embodiment of a record that has been purchased or accepted by a realtor-client. As with record 1600, all pertinent information regarding the qualified lead or scheduled appointment may be provided. Additionally, different functions may be implemented such the call and email launching functions mentioned above. In the embodiment shown an interface for communicating with the interested party is also included with the GUI; again this may be helpful for the service provider to track actions taken by the realtor-client (although not necessarily the contents of the communication).

Figure 23:
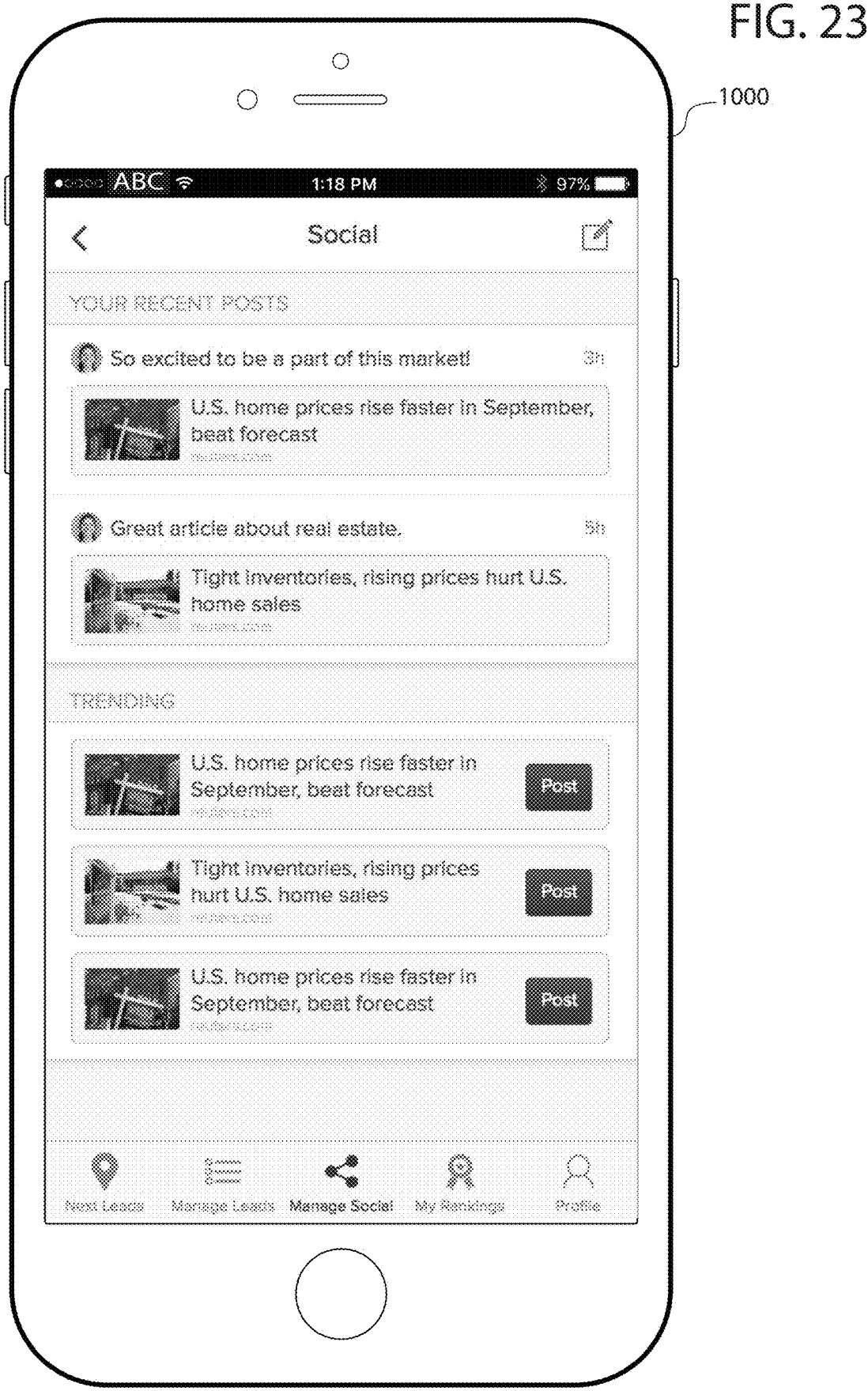
FIG. 23 illustrates an exemplary social media platform provided via the user interface, in accordance with one embodiment of the present invention.

FIG. 23 illustrates an exemplary social media platform provided via the user interface, in accordance with one embodiment of the present invention. A realtor-client may access this screen by selecting "MANAGE MY SOCIAL" from the dashboard. Post, manage and send listings to all social sites can be enabled from this screen. These functionalities may facilitate realtor-clients to view their prior posts/currently on their social sites, and even research trending articles.

Figure 24:
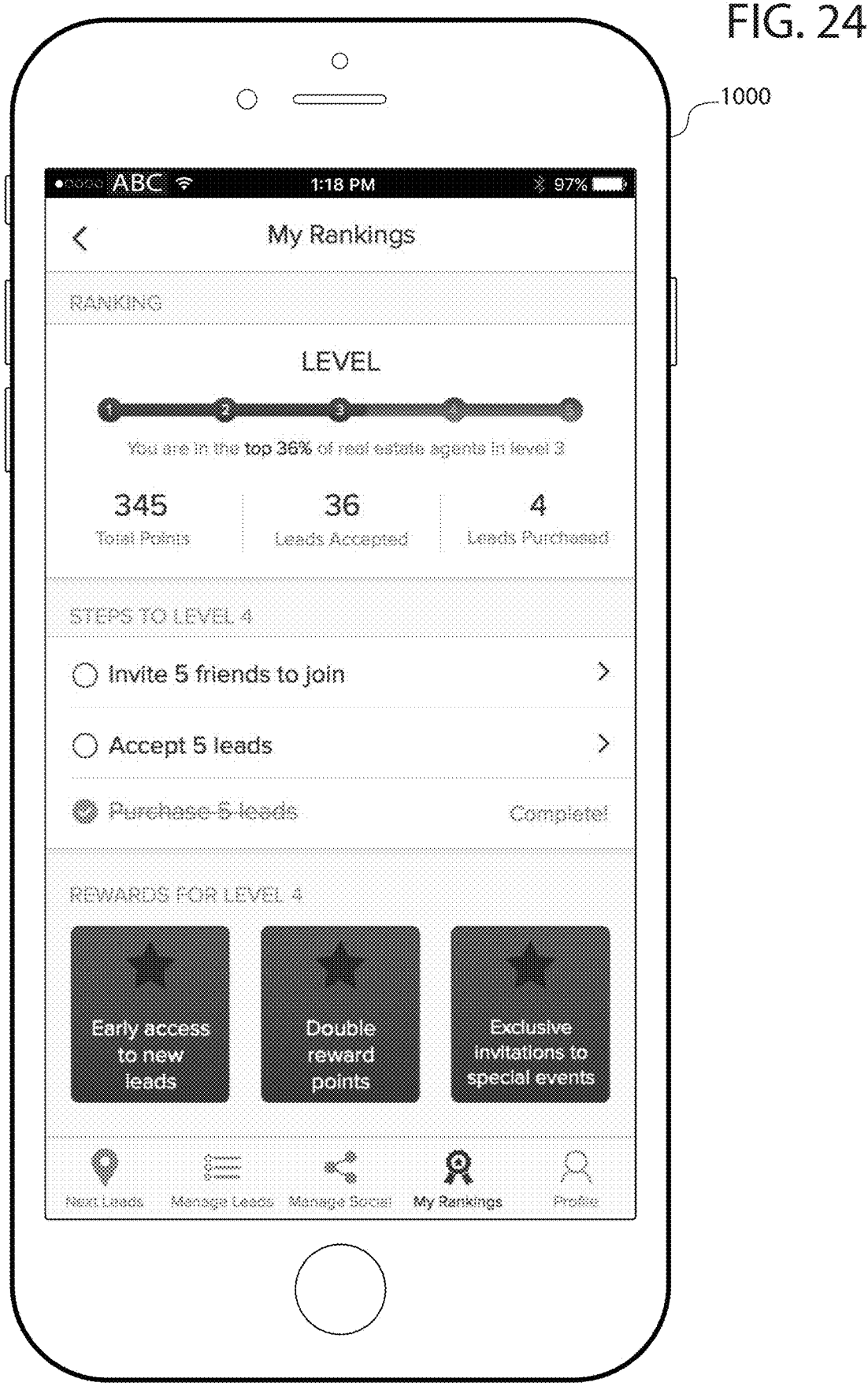
FIG. 24 illustrates an exemplary user interface, which implements an incentive-based algorithm, in accordance with one embodiment of the present invention.

Finally, FIG. 24 illustrates an exemplary user interface, which implements an incentive-based algorithm, in accordance with one embodiment of the present invention. A realtor-client may access this screen by selecting "MY RANKINGS" from the dashboard. In exemplary embodiments, the incentive-based algorithm may provide incentives such as earning credit and ranking by using the mobile application. The idea is to engage the realtor-client, develop best practices and provide rewards or incentives for data sharing and proactive realtor management. Moreover, data provided by realtor-clients can be recycled or utilized by the service provider—effectively utilizing clients of the system as an additional source of data, which may be in turn provided back to realtor-clients to take advantage of the transactional opportunities generated from that data.

Although the transactional opportunities that the system described above focus on real estate transactions, other applications in other fields may just as easily be implemented. For example, and without deviating from the scope of the present invention, a system and method such as the one described above may be practice with respect to mortgages, contractors, inspection services, or other fields in which scheduled appointments are key to consummating a transaction.

A system and method for transacting scheduled appointments has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

What is claimed is:

1. A graphical user interface (GUI) distributed to a plurality of client devices for transacting a scheduled appointment record, the GUI comprising:
    a first screen automatically launched in response to receiving a notification from a server concerning an offer record, the first screen displaying:
        an acceptance button, and
        offer information associated with the offer record, the offer information excluding identification or contact information of an interested party associated with the offer record, wherein the offer record is associated with the scheduled appointment record, the scheduled appointment record including: a lead price for the offer record that is established based on a value of a prospect for consummating a proposed transaction at a previously scheduled meeting at a specific date and a specific time agreed-to by the interested party to discuss the proposed transaction with at least one user associated with one of the plurality of client devices; and
    a second screen launched in response to a user pressing the acceptance button on the first screen indicative of a purchase of the offer record by the user, the purchase of the offer record indicating an acceptance of the lead price in exchange for an opportunity to meet the interested party at the specific date and the specific time agreed-to by the interested party, wherein the second screen displays an identification or contact information of the interested party associated with the offer record.

2. The GUI of claim 1, further comprising:
    a third screen displaying a map layout including one or more indicators associated with one or more offer records concerning lead records offered to the user of the client device.

3. The GUI of claim 2, wherein the one or more indicators comprise of:
    color-coded indicators indicative of one or more categories for each of the one or more offer records, each of the one or more categories defined by a lead tier protocol indicative of a lead price of the one or more offer records.

4. The GUI of claim 2, wherein the one or more indicators comprise of:
    shape-coded indicators indicative of one or more categories for each of the one or more offer records, each of the one or more categories defined by a lead tier protocol indicative of a lead price of the one or more offer records.

5. The GUI of claim 1, further comprising:
    a third screen displaying a dashboard with one or more tabs configured to navigate the user to one or more lead management tools.

6. The GUI of claim 5, wherein the one or more lead management tools includes a category filtering tool for enabling or disabling a view of one or more categories of offer records.

7. The GUI of claim 5, wherein the one or more lead management tools includes a price range tool for viewing offer records associated with properties within a selectable price range.

8. The GUI of claim 5, wherein the one or more lead management tools includes a square footage tool for viewing offer records associated with properties including a selectable square footage range.

9. The GUI of claim 5, wherein the one or more lead management tools includes a bedroom selection tool for viewing offer records associated with properties including a selectable number of bedrooms range.

10. The GUI of claim 5, wherein the one or more lead management tools includes a bathroom selection tool for viewing offer records associated with properties including a selectable number of bathrooms range.

11. The GUI of claim 1, wherein the offer record comprises a time-sensitive offer record and the first screen within the GUI further comprises a count-down clock.

12. The GUI of claim 1, wherein the purchase of the offer record from the client device comprises a successful bid for the offer record via the client device.

13. The GUI of claim 1, wherein the second screen further displays the specific date and the specific time agreed-to by the interested party.

14. The GUI of claim 1, wherein the second screen further displays a blurred contact information, and the second screen further displays a revealed contact information.

15. The GUI of claim 1, wherein the second screen further displays a disabled contact button, and the second screen further displays an enabled contact button.

16. A method, performed by a server and a plurality of client devices, for displaying and transacting a scheduled appointment record by way of a graphical user interface (GUI) distributed to the plurality of client devices, comprising:

generating, by the server, an offer record associated with the scheduled appointment record, the scheduled appointment record including: a lead price for the offer record that is established based on a value of a prospect for consummating a proposed transaction at a previously scheduled meeting at a specific date and a specific time agreed-to by an interested party to discuss the proposed transaction with at least one user associated with one of the plurality of client devices;

transmitting, by the server via a network, the offer record to a client device configured to execute the GUI, wherein the client device automatically launches a first screen within the GUI in response to receiving the offer record, the first screen within the GUI displaying:
an acceptance button, and
offer information associated with offer record, the offer information excluding identification or contact information of the interested party; and transmitting, by the client device via the network, a purchase of the offer record by a user of the client device in response to the user of the client device pressing the acceptance button, the purchase of the offer record indicating an acceptance of the lead price in exchange for an opportunity to meet the interested party at the specific date and the specific time agreed-to by the interested party;

wherein the client device launches a second screen within the GUI in response to the user pressing the acceptance button, the second screen within the GUI displaying an identification or contact information of the interested party associated with the offer record.

17. The method of claim 16, wherein transmitting the offer record to the client device comprises:
receiving a role identification concerning a membership status associated with the client device; and
delivering the offer record to the client device if the membership status authorizes access to the scheduled appointment record.

18. The method of claim 16, further comprising monitoring a progress status associated with the proposed transaction, including:
receiving an indication of an action initiated from the client device concerning a meeting between the user and the interested party that occurs on the specific date and the specific time; and
sending a request to the client device in response to the indication of the action.

19. The method of claim 16, further comprising:
triggering, by the server in response to receiving the purchase of the offer record from the client device, a first predetermined time period assigned to the offer record;
receiving by the server, a progress status associated with the proposed transaction from the client device via the network;
determining, by the server, whether the first predetermined time period has lapsed prior to a consummation of the proposed transaction; and
either:
registering, by the server with the client device, the consummation of the proposed transaction; or
triggering, by the server, a second predetermined time period if the first predetermined time period has lapsed prior to the consummation of the proposed transaction.

20. The method of claim 19, wherein the client device is a first client device and the method further comprises:
generating a second offer record associated with the scheduled appointment record, if the first predetermined time period has lapsed prior to the consummation of the proposed transaction;
providing the second offer record to a second client device;
registering a purchase of the second offer record with the second client device; and
monitoring, via the second client device, the progress status associated with the proposed transaction.

* * * * *